(12) United States Patent
Lai et al.

(10) Patent No.: US 10,744,213 B2
(45) Date of Patent: Aug. 18, 2020

(54) FLUORESCENT COMPOUNDS FOR IMAGING OF BLOOD VESSELS AND BLOOD FLOW, AND AN IN VIVO SCREEN FOR PRO- AND ANTI-ANGIOGENIC AGENTS

(71) Applicant: Jose Mendoza, Chapel Hill, NC (US)

(72) Inventors: Yen-Shi Lai, Chapel Hill, NC (US); Chien-Hsin Pan, Tainan (TW); Yu-Ting Lo, New Taipei (TW); Siao-Ping Huang, Tainan (TW); I-Wen Wang, Chiayi (TW); Jose Mendoza, Chapel Hill, NC (US)

(73) Assignee: COLOSSUS BIOPHARMA CONSULTANTS COMPANY, LIMITED, Kaohsiung (TW)

( * ) Notice: Subject to any disclaimer, the term of this patent is extended or adjusted under 35 U.S.C. 154(b) by 449 days.

(21) Appl. No.: 15/432,291

(22) Filed: Feb. 14, 2017

(65) Prior Publication Data

US 2018/0228923 A1    Aug. 16, 2018

(51) Int. Cl.
| | | |
|---|---|---|
| *A61K 49/00* | (2006.01) | |
| *A61B 5/00* | (2006.01) | |
| *A61B 5/02* | (2006.01) | |
| *A61B 5/026* | (2006.01) | |

(52) U.S. Cl.
CPC ........ *A61K 49/0039* (2013.01); *A61B 5/0071* (2013.01); *A61B 5/0261* (2013.01); *A61B 5/489* (2013.01); *A61B 2503/42* (2013.01)

(58) Field of Classification Search
None
See application file for complete search history.

(56) References Cited

U.S. PATENT DOCUMENTS

2009/0010849 A1*  1/2009  McGrath ............ A61K 49/0008
                                                424/9.2

OTHER PUBLICATIONS

Heylin, M., et al., "Chemistry Grads Post Gains in 2005", C and EN, pp. 43-52 (Year: 2006).*
Dorwald, F.Z., et al., "Side Reactions in Organic Synthesis", Wiley VCH Verlag, p. IX (Year: 2005).*
Miyauchi, T., et al., "Waon Therapy Upregulates Hsp90 and Leads to Angiogenesis Through the Akt-Endothelial Nitric Oxide Synthase Pathway in Mouse Hindlimb Ischemia", Circulation Journal, pp. 1712-1721 (Year: 2012).*
Bai, S., Y., et al., "Discovery of a novel fluorescent HSP90 inhibitor and its anti-lung cancer effect", RSC Advances, pp. 19887-19890 (Year: 2014).*
Toxnet, "1H-1,2,4-Triazole", accessed from: https://toxnet.nlm.nih.gov/cgi-bin/sis/search/a?dbs+hsdb:@term+@DOCNO+7860, printed on Jun. 2019, pp. 1-12 (Year: 2019).*
Durjava, M.K., et al., "Experimental Assessment of the Environmental Fate and Effects of Triazoles and Benzotriazole", ATLA, pp. 65-75 (Year: 2013).*

* cited by examiner

*Primary Examiner* — Michael G. Hartley
*Assistant Examiner* — Lance W Rider

(57) ABSTRACT

The present invention discloses fluorescent compounds and a method for their use for selective imaging of blood vessels and blood flow. By applying these fluorescent compounds and the imaging process to a zebrafish model, the present invention further provides methods and procedures for the discovery, selection, and characterization of pro- and anti-angiogenic agents.

3 Claims, 4 Drawing Sheets

(a) Control (b) Treatment with 1µM Sunitinib (c) Treatment with 2.5µM Sunitinib (d) Treatment with 5µM Sunitinib (a) Before fluorescent staining (b) After fluorescence staining

5-Day Acute Toxicity on Zebrafish

| | 0 | 1 | 2 | 3 | 4 | 5 |
|---|---|---|---|---|---|---|
| 350µM | 100 | 100 | 100 | 0 | 0 | 0 |
| 325µM | 100 | 100 | 100 | 70 | 20 | 10 |
| 300µM | 100 | 100 | 100 | 80 | 30 | 20 |
| 275µM | 100 | 100 | 100 | 100 | 80 | 50 |
| 250µM | 100 | 100 | 100 | 100 | 90 | 80 |
| 225µM | 100 | 100 | 100 | 100 | 100 | 100 |
| 0.5%DMSO | 100 | 100 | 100 | 100 | 100 | 100 |

Probit Model, with BMR of 50% Extra Risk for the BMD and 0.95 Lower Confidence Limit for the BMDL

FLUORESCENT COMPOUNDS FOR IMAGING OF BLOOD VESSELS AND BLOOD FLOW, AND AN IN VIVO SCREEN FOR PRO- AND ANTI-ANGIOGENIC AGENTS

CROSS REFERENCE

The priority of this application is a U.S. provisional application 62/295,503 filed Feb. 16, 2016.

BACKGROUND OF THE INVENTION

Real time imaging of blood vessels that reveals the structure and hemodynamics of the vascular system has a variety of biomedical applications (see, for example, Makale, M., Methods in Enzymology 2008, 444, 175-199; Ghaffari, S., Development 2015, 142, 4158-4167; Sahn, D. and Vick, G., Heart 2001, 86 (Supp) II), ii41-ii53). Several imaging technologies are currently available for these applications (for a review, see Upputuri, P., BioMed Research International, 2015, Article ID 783983, and references therein). However, they all suffer from one or more of a number of disadvantages such as equipment cost, complicated procedure, harmful exposure of test subjects to high energy, long scanning and post-process time, or insufficient resolution. These limitations are particularly prohibitory against large-scale use on animals in preclinical studies. A quick, easy-to-operate, low cost, and high resolution vasculature imaging technology, applicable to live animals, i.e. being vital, in particular, is not only a desirable improvement for clinical applications, but will prove highly useful for studying human diseases in animal models.

The value of such technologies is well demonstrated in cancer. Angiogenesis is a hallmark of cancer in which tumor cells in patients recruit new blood vessels to supply nutrients for tumor growth and metastasis (see Carmeliet, P. and Jain, R., Nature 2000, 407, 249-257). Therefore, detection, monitoring, and inhibition of angiogenesis surrounding cancer cells play a critical role in our fight against cancer. In the area of anti-cancer therapy development, there is continuous interest in tools and methods that characterize the occurrence of angiogenesis and enable the discovery of agents that inhibit or promote angiogenesis and thus tumor progression.

In vitro assays are available to examine pro- and anti-angiogenic substances (see, for examples, Ngo, T. et. al., International Journal of Tissue Regeneration 2014, 5(2), 37-45; Ucuzian, A and Greisler, H., World J. Surg. 2007, 31, 654-663). These assays are designed to mimic the in vivo environment. However, their adequacy is open to debate and the results from these assays always require confirmation in vivo.

In vivo assays for angiogenesis that use a specific part or system of live animals also have a long history of development. These models are mostly performed on rodent or larger animals, such as dogs, and can be prohibitively expensive. They are all technically cumbersome due to the need for surgery and the operations are often time consuming (see Norrby, K., J. Cell. Mol. Med. 2006, 10(3), 588-612).

Whole animal models have been developed to study angiogenesis using zebrafish (*Danio rerio*), the *Xenopus Laevis* tadpole, and more recently the invertebrate Hirudo medicinalis (see, for example, Ny, A. et. al., Experimental Cell Research 2006, 312, 684-693). For reasons highlighted in the following, the zebrafish models have stood out in particular, in terms of practicality, for the research on angiogenesis and its modulators.

First of all, approximately 70% of all human protein-coding genes have functional homologs in zebrafish (see Howe, K. et. al., Nature 2013, 496, 498-503). Each mating pair of zebrafish produces hundreds of offspring per week, making embryos readily available for large scale phenotypic screening. Zebrafish embryos and early larvae are virtually transparent which makes visualization of its tissues and organs feasible. These and other features have placed zebrafish high on the list of model animals available for the investigation of human diseases and for the discovery of potential therapeutic drugs in general (see, for example, Lieschke, G. and Currie, P., Nature Reviews Genetics 2007, 8, 353-367; Santoriello, C. and Zon, L., J. Clin. Invest. 2012, 122(7), 2337-2343).

The vascular anatomy of developing zebrafish embryo has been described in detail. In addition to a high structural homology to other vertebrates, the molecular mechanisms underlying vessel formation in zebrafish are highly similar to those in humans and other higher vertebrates (see Isogai, S. et. al., Developmental Biology 2001, 230, 278-301). Early analysis of vascular pattern in zebrafish was performed by microinjection of dyes or small fluorescent microspheres into the blood vessels. The injection is difficult to perform due to the size of embryos, and mature vascular lumenization and connection to the circulation are required for the method to work. Imaging of zebrafish blood vessels can also be done by staining for endogenous alkaline phosphatase (AP) activity in vascular endothelium, but only within a fix development window when the AP signal is high relative to background staining. All these methods are performed after specimen fixation; they are not vital and cannot be used to show the dynamics of vessel development or blood flow (see Kamei, M. et. al., Methods in Cell Biology 2010, 100, 27-54).

So far, the most convenient vital imaging of zebrafish vascular system relies on expression of vascular specific transgenic fluorophores. Numerous transgenic zebrafish lines have been engineered and generated that express a vascular specific gene with green fluorescence protein as a reporter in related tissues for the visualization and study of zebrafish vascular development (see Chavez, M. et. al., Front. Physiol. 2016, 7, article 56). These mutant fishes have been widely used to study the effect of treatments on the development of blood vessels. The drawback is that the fluorescence is inherited and permanent once developed. And the results cannot be related to wild type without the inherent risks of using inference.

RELEVANT LITERATURE REFERENCES

The following reference may be helpful to the reader while considering the invention taught herein:
In vivo angiogenesis assay (U.S. Pat. No. 1995/5,382,514);
In vivo assay for anti angiogenic compounds (PCT Int. Appl. (2002), WO 02/098469 A1);
In vivo angiogenesis assay (U.S. Pat. Appl. 2006/0165595 A1);

BRIEF SUMMARY OF THE INVENTION

The present invention relates to fluorescent compounds useful for the visualization and imaging of blood vessels and blood flow in tissues, as well as in whole animals. In further application, the imaging process and the resultant fluorescence images of this invention form the basis of a method directed to the rapid identification, selection and characterization of substances capable of interfering with the blood vessel formation process, or angiogenesis as used interchangeably in this invention. Such substances are valuable for someone intending to develop therapeutic agents against a disease related to angiogenesis. Examples of diseases or conditions that can benefit from the embodiments of this invention include but are not limited to, cancer, diabetes, wound management, and peripheral arterial diseases. A fluorescent compound according to the present invention is a molecule capable of absorbing light energy, or being excited, at one wavelength and nearly instantaneously re-emitting at another, usually longer, wavelength. However, it is understood that the wavelength characteristics of fluorescent compounds can be altered, for example, by changing the number of conjugated pi-bonds responsible for the fluorescence phenomenon. In general, the longer the conjugated pi-bond system is, the higher the wavelengths of excitation and emission are. The emission wavelengths of fluorescent compounds according to this invention range from about 300 nanometers to about 1,000 nanometers.

Thus, in a first aspect, the present invention concerns compounds of formula I:

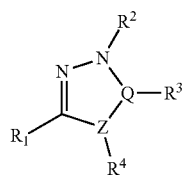

Wherein;
$R^1$, $R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;
Q-Z is either C—C, C=C, C—N, C=N, N—C, or N=C; and pharmaceutically acceptable salts, solvates, chelates, non-covalent complexes, prodrugs, and mixtures thereof, including both R and S enantiomeric forms and racemic mixtures thereof.

A particular embodiment of the compound of Formula I is a compound of Formula II:

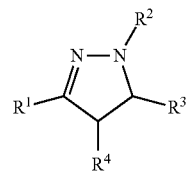

Wherein;
$R^1$, $R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro.

A particular embodiment of the compound of Formula II is a compound of Formula III:

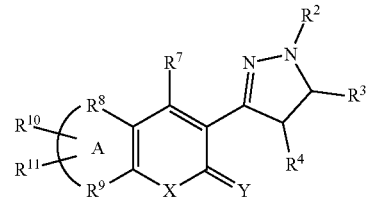

Wherein;
$R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

$R^7$ is independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, oxo and nitro; wherein $R^5$ and $R^6$ are being defined above;

X and Y are independently chosen from nitrogen, oxygen, or sulfur;

Wherein A is Fe and $R^9$ taken together to form a substituted or unsubstituted saturated or unsaturated, aromatic or non-aromatic, 3-8 membered monocyclic ring, or 8-12 bicyclic membered ring, having 0-3 heteroatoms independently selected from nitrogen, oxygen, or sulfur; substituted or unsubstituted, unsaturated or partially unsaturated monocyclic or bicyclic 5-12 membered ring, or a substituted or unsubstituted aryl or heteroaryl ring;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A particular embodiment of the compound of Formula III is a compound of Formula IV:

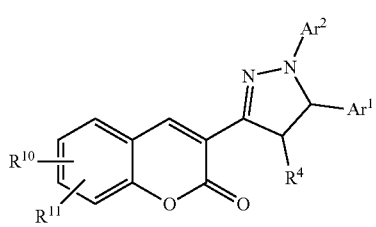

IV

Wherein;

$Ar^1$ and $Ar^2$ are independently selected from aryl or heteroaryl optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

$R^4$ is independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, halogen, cyano, and nitro;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro.

A specific embodiment of a compound of Formula IV is a compound selected from the following group:

1) 4-(3-(6-Methoxy-2-oxo-2H-chromen-3-yl)-5-phenyl-4,5-dihydro-1H-pyrazol-1-yl)benzoic acid,
2) 4-(3-(7-(3-Bromopropoxy)-2-oxo-2H-chromen-3-yl)-5-phenyl-4,5-dihydro-1H-pyrazol-1-yl)benzoic acid,
3) (11-((4-(3-(6-Methoxy-2-oxo-2H-chromen-3-yl)-5-phenyl-4,5-dihydro-1H-pyrazol-1-yl)benzoyl)oxy)undecyl) triphenylphosphonium,
4) Ethyl 4-(3-(6-methoxy-2-oxo-2H-chromen-3-yl)-5-phenyl-4,5-dihydro-1H-pyrazol-1-yl)benzoate
5) 5-Chloropentyl 4-(3-(6-methoxy-2-oxo-2H-chromen-3-yl)-5-phenyl-4,5-dihydro-1H-pyrazol-1-yl)benzoate,
6) (3R,4R,5S,6R)-6-(Acetoxymethyl)-3-(4-(3-(6-methoxy-2-oxo-2H-chromen-3-yl)-5-phenyl-4,5-dihydro-1H-pyrazol-1-yl)benzamido)tetrahydro-2H-pyran-2,4,5-triyl triacetate,
7) 4-(3-(6-Methoxy-2-oxo-2H-chromen-3-yl)-1-phenyl-4,5-dihydro-1H-pyrazol-5-yl)benzoic acid,
8) (3-((3-(1-(4-Carboxyphenyl)-5-phenyl-4,5-dihydro-1H-pyrazol-3-yl)-2-oxo-2H-chromen-7-yl)oxy)propyl)triphenylphosphonium,
9) Ethyl 4-(3-(6-methoxy-2-oxo-2H-chromen-3-yl)-1-phenyl-4,5-dihydro-1H-pyrazol-5-yl)benzoate,
10) 2,5-Dioxopyrrolidin-1-yl 4-(3-(6-methoxy-2-oxo-2H-chromen-3-yl)-5-phenyl-4,5-dihydro-1H-pyrazol-1-yl) benzoate,
11) 4-(3-(6-Methoxy-2-oxo-2H-chromen-3-yl)-5-phenyl-4,5-dihydro-1H-pyrazol-1-yl)-N-((3R,4R,5S,6R)-2,4,5-trihydroxy-6-(hydroxymethyl)tetrahydro-2H-pyran-3-yl) benzamide, 12) 3-(1-(4-Fluorophenyl)-5-phenyl-4,5-dihydro-1H-pyrazol-3-yl)-6-methoxy-2H-chromen-2-one,
13) (3-((4-(3-(6-Methoxy-2-oxo-2H-chromen-3-yl)-1-phenyl-4,5-dihydro-1H-pyrazol-5-yl)benzoyl)oxy)propyl)triphenylphosphonium,
14) (Z)-5-(((5-Fluoro-2-oxoindolin-3-ylidene)methyl)-N-(2-(4-(3-(6-methoxy-2-oxo-2H-chromen-3-yl)-5-phenyl-4,5-dihydro-1H-pyrazol-1-yl)benzamido)ethyl)-2,4-dimethyl-1H-pyrrole-3-carboxamide,
15) Diethyl 4,4'-(3-(6-methoxy-2-oxo-2H-chromen-3-yl)-4,5-dihydro-1H-pyrazole-1,5-diyl)dibenzoate,
16) 3-(2-(5-(((3aS,4S,6aR)-2-Oxohexahydro-1H-thieno[3,4-d]imidazol-4-yl)pentanoyl)hydrazinyl)propyl 4-(3-(6-methoxy-2-oxo-2H-chromen-3-yl)-5-phenyl-4,5-dihydro-1H-pyrazol-1-yl)benzoate hydrochloride,
17) 3-Bromopropyl 4-(3-(6-methoxy-2-oxo-2H-chromen-3-yl)-1-phenyl-4,5-dihydro-1H-pyrazol-5-yl)benzoate,
18) (Z)-3-((2-(5-(((5-Fluoro-2-oxoindolin-3-ylidene)methyl)-2,4-dimethyl-1H-pyrrole-3-carboxamido)ethyl)amino)propyl 4-(3-(6-methoxy-2-oxo-2H-chromen-3-yl)-5-phenyl-4,5-dihydro-1H-pyrazol-1-yl)benzoate hydrochloride,
19) 4-(5-(4-(Ethoxycarbonyl)phenyl)-3-(6-methoxy-2-oxo-2H-chromen-3-yl)-4,5-dihydro-1H-pyrazol-1-yl)benzoic acid,
20) 4-(3-(6-Methoxy-2-oxo-2H-chromen-3-yl)-5-phenyl-4,5-dihydro-1H-pyrazol-1-yl)-N'-(5-((3aS,4S,6aR)-2-oxohexahydro-1H-thieno[3,4-d]imidazol-4-yl)pentanoyl)benzohydrazide,
21) Ethyl 4-(5-(3,4-dimethoxyphenyl)-3-(6-methoxy-2-oxo-2H-chromen-3-yl)-4,5-dihydro-1H-pyrazol-1-yl)benzoate, and
22) Ethyl 3-(7-hydroxy-2-oxo-2H-chromen-3-yl)-1,5-diphenyl-4,5-dihydro-1H-pyrazole-4-carboxylate.

A particular embodiment of the compound of Formula II is a compound of Formula V:

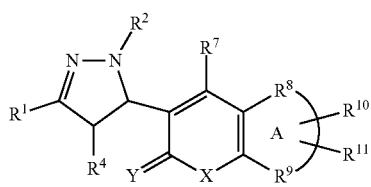

V

Wherein;
$R^1$, $R^2$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;
Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;
$R^7$ is independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro; wherein $R^5$ and $R^6$ are being defined above;
X and Y are independently chosen from nitrogen, oxygen, or sulfur;
Wherein A is $R^8$ and $R^9$ taken together to form a substituted or unsubstituted saturated or unsaturated, aromatic or non-aromatic, 3-8 membered monocyclic ring, or 8-12 bicyclic membered ring, having 0-3 heteroatoms independently selected from nitrogen, oxygen, or sulfur; substituted or unsubstituted, unsaturated or partially unsaturated monocyclic or bicyclic 5-12 membered ring, or a substituted or unsubstituted aryl or heteroaryl ring;
$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A particular embodiment of the compound of Formula V is a compound of Formula VI:

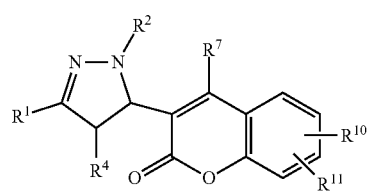

VI

Wherein;
$R^1$, $R^2$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, C(O)R$^6$, C(O)OR$^5$, C(O)NR$^5$R$^6$, NR$^5$C(O)R$^6$, NR$^5$C(O)OR$^6$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

R$^7$ is independently selected from hydrogen, halogen, nitro, cyano, OR$^5$, OC(O)R$^5$, NR$^5$R$^6$, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro; wherein R$^5$ and R$^6$ are being defined above;

R$^{10}$ and R$^{11}$ are independently selected from hydrogen, halogen, nitro, cyano, OR$^5$, OC(O)R$^5$, NR$^5$R$^6$, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro.

A particular embodiment of the compound of Formula VI is a compound of Formula VII:

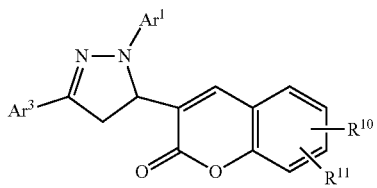

VII

Wherein;
Ar$^1$ and Ar$^3$ are independently selected from aryl or heteroaryl optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

R$^{10}$ and R$^{11}$ are independently selected from hydrogen, halogen, nitro, cyano, OR$^5$, OC(O)R$^5$, NR$^5$R$^6$, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro.

A specific embodiment of a compound of Formula VII is a compound selected from the following group:
23) Ethyl 4-(5-(7-hydroxy-2-oxo-2H-chromen-3-yl)-3-phenyl-4,5-dihydro-1H-pyrazol-1-yl)benzoate, and
24) Ethyl 4-(5-(7-(3-bromopropoxy)-2-oxo-2H-chromen-3-yl)-3-phenyl-4,5-dihydro-1H-pyrazol-1-yl)benzoate.

Another particular embodiment of the compound of Formula II is a compound of Formula VIII:

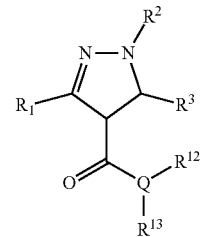

VIII

Wherein;
R$^1$, R$^2$, and R$^3$ are independently selected from hydrogen, alkyl, substituted saturated or unsaturated alkyl, S(O)$_{1-2}$R$^5$, SO$_2$NR$^5$R$^6$, C(O)R$^5$, C(O)OR$^5$, and C(O)NR$^5$R$^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

Q is independently chosen from nitrogen or oxygen;

$R^{12}$ and $R^{13}$ are independently selected from hydrogen, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

and pharmaceutically acceptable salts, solvates, chelates, non-covalent complexes, prodrugs, and mixtures thereof, including both R and S enantiomeric forms and racemic mixtures thereof.

A particular embodiment of the compound of Formula VIII is a compound of Formula IX:

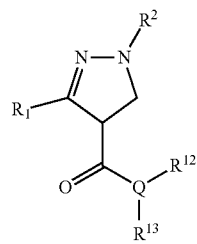

IX

Wherein;
$R^1$ and $R^2$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)$ $R^6$, $NR^5C(O)OR^6$, $R^5P(R^6)_3$, halogen, cyano, and nitro;

Q is independently chosen from nitrogen or oxygen;
$R^{12}$ and $R^{13}$ are independently selected from hydrogen, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A specific embodiment of a compound of Formula IX is a compound selected from the following group:
25) N-Benzyl-1,3-diphenyl-4,5-dihydro-1H-pyrazole-4-carboxamide,
26) Ethyl 1-(4-fluorophenyl)-3-phenyl-4,5-dihydro-1H-pyrazole-4-carboxylate, and
27) 4-(4-(Ethoxycarbonyl)-3-phenyl-4,5-dihydro-1H-pyrazol-1-yl)benzoic acid.

Another particular embodiment of the compound of Formula I is a compound of Formula X:

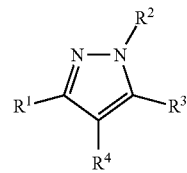

X

Wherein;
$R^1$, $R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)$ $R^6$, $NR^5C(O)OR^6$, $R^5P(R^6)_3$, halogen, cyano, and nitro;

and pharmaceutically acceptable salts, solvates, chelates, non-covalent complexes, prodrugs, and mixtures thereof, including both R and S enantiomeric forms and racemic mixtures thereof.

A particular embodiment of the compound of Formula X is a compound of Formula XI:

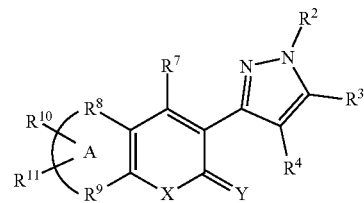

XI

Wherein;

$R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

$R^7$ is independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, oxo and nitro; wherein $R^5$ and $R^6$ are being defined above;

X and Y are independently chosen from nitrogen, oxygen, or sulfur;

Wherein A is $R^8$ and $R^9$ taken together to form a substituted or unsubstituted saturated or unsaturated, aromatic or non-aromatic, 3-8 membered monocyclic ring, or 8-12 bicyclic membered ring, having 0-3 heteroatoms independently selected from nitrogen, oxygen, or sulfur; substituted or unsubstituted, unsaturated or partially unsaturated monocyclic or bicyclic 5-12 membered ring, or a substituted or unsubstituted aryl or heteroaryl ring;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A particular embodiment of the compound of Formula XI is a compound of Formula XII:

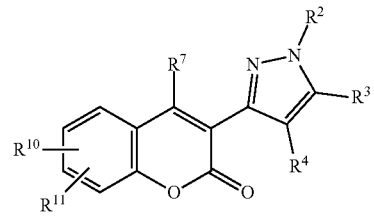

XII

Wherein;

$R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

$R^7$ is independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro; wherein $R^5$ and $R^6$ are being defined above;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A particular embodiment of the compound of Formula XII is a compound of Formula XIII:

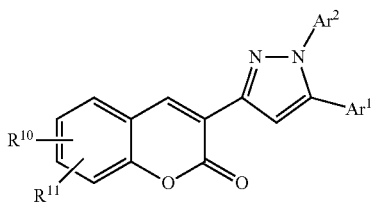

XIII

Wherein;
$Ar^1$ and $Ar^2$ are independently selected from aryl or heteroaryl optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;
$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;
  Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A specific embodiment of a compound of Formula XIII is a compound selected from the following group:
28) Ethyl 4-(3-(6-methoxy-2-oxo-2H-chromen-3-yl)-1-phenyl-1H-pyrazol-5-yl)benzoate,
29) 3-(5-(3,4-Dimethoxyphenyl)-1-phenyl-1H-pyrazol-3-yl)-6-methoxy-2H-chromen-2-one, and
30) 4-(5-([1,1'-Biphenyl]-4-yl)-3-(6-methoxy-2-oxo-2H-chromen-3-yl)-1H-pyrazol-1-yl)benzoic acid.

A particular embodiment of the compound of Formula X is a compound of Formula XIV:

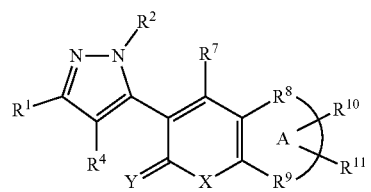

XIV

Wherein;
$R^1$, $R^2$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;
  Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

$R^7$ is independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro; wherein $R^5$ and $R^6$ are being defined above;

X and Y are independently chosen from nitrogen, oxygen, or sulfur;

Wherein A is Fe and $R^9$ taken together to form a substituted or unsubstituted saturated or unsaturated, aromatic or non-aromatic, 3-8 membered monocyclic ring, or 8-12 bicyclic membered ring, having 0-3 heteroatoms independently selected from nitrogen, oxygen, or sulfur; substituted or unsubstituted, unsaturated or partially unsaturated monocyclic or bicyclic 5-12 membered ring, or a substituted or unsubstituted aryl or heteroaryl ring;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A particular embodiment of the compound of Formula XIV is a compound of Formula XV:

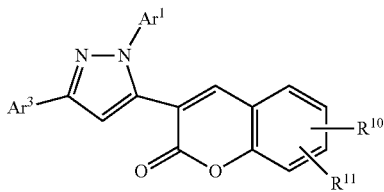

Wherein;

Ar$^1$ and Ar$^2$ are independently selected from aryl or heteroaryl optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

R$^{10}$ and R$^{11}$ are independently selected from hydrogen, halogen, nitro, cyano, OR$^5$, OC(O)R$^5$, NR$^5$R$^6$, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro.

A specific embodiment of a compound of Formula XV is a compound selected from the following group:

31) Ethyl 4-(5-(7-hydroxy-2-oxo-2H-chromen-3-yl)-3-phenyl-1H-pyrazol-1-yl)benzoate.

Another particular embodiment of the compound of Formula X is a compound of Formula XVI:

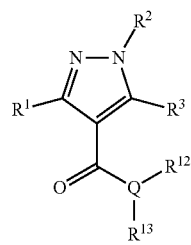

Wherein;

R$^1$, R$^2$, and R$^3$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

Q is independently chosen from nitrogen, oxygen, or sulfur;

R$^{12}$ and R$^{13}$ are independently selected from hydrogen, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro.

A particular embodiment of the compound of Formula XVI is a compound of Formula XVII:

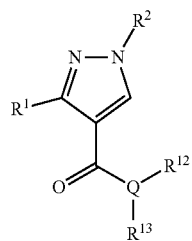

Wherein;

R$^1$ and R$^2$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

Q is independently chosen from nitrogen or oxygen;

$R^{12}$ and $R^{13}$ are independently selected from hydrogen, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A specific embodiment of a compound of Formula XVII is a compound selected from the following group:

32) Ethyl 1,3-diphenyl-1H-pyrazole-4-carboxylate,
33) 5-((1,3-Diphenyl-1H-pyrazole-4-carboxamido)methyl)-1-ethyl-2-((1E,3E)-3-(1-ethyl-3,3-dimethylindolin-2-ylidene)prop-1-en-1-yl)-3,3-dimethyl-3H-indol-1-ium,
34) Ethyl 1-(4-fluorophenyl)-3-phenyl-1H-pyrazole-4-carboxylate, and
35) N-Benzyl-1-(4-fluorophenyl)-3-phenyl-1H-pyrazole-4-carboxamide.

Another particular embodiment of the compound of Formula X is a compound of Formula XVIII:

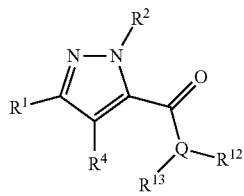

XVIII

Wherein;

$R^1$, $R^2$, and $R^4$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

Q is independently chosen from nitrogen or oxygen;

$R^{12}$ and $R^{13}$ are independently selected from hydrogen, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

A specific embodiment of a compound of Formula XVIII is a compound selected from the following group:

36) 4-Chloro-6-(4-(4-methoxyphenyl)-5-methyl-1H-pyrazol-3-yl)benzene-1,3-diol,
37) 3-(5-Chloro-2,4-dihydroxyphenyl)-4-(4-methoxyphenyl)-1H-pyrazole-5-carboxylic acid,
38) 3-(5-Chloro-2,4-dihydroxyphenyl)-4-(4-methoxyphenyl)-N-phenyl-1H-pyrazole-5-carboxamide,
39) 3-(5-Chloro-2,4-dihydroxyphenyl)-N-(3-((3-(3-fluorophenyl)-2-oxo-2H-chromen-7-yl)oxy)propyl)-4-(4-methoxyphenyl)-1H-pyrazole-5-carboxamide, and
40) 5-((3-(5-Chloro-2,4-dihydroxyphenyl)-4-(4-methoxyphenyl)-1H-pyrazole-5-carboxamido)methyl)-1-ethyl-2-((1E,3E)-3-(1-ethyl-3,3-dimethylindolin-2-ylidene)prop-1-en-1-yl)-3,3-dimethyl-3H-indol-1-ium,
41) Ethyl 1-(4-(benzylcarbamoyl)phenyl)-3-phenyl-4,5-dihydro-1H-pyrazole-4-carboxylate, and
42) Sodium 1-(4-(benzylcarbamoyl)phenyl)-3-phenyl-4,5-dihydro-1H-pyrazole-4-carboxylate.

In a second aspect, the present invention concerns the use of the fluorescent compounds, described in accordance with the first aspect of this invention, to visualize and image blood vessels, as well as the motion of blood flow when applicable, in a test subject.

In one embodiment of this aspect, the fluorescent compounds are administered to interact with blood vessels and/or blood serum in a test subject. The test subject can be a part, such as a tissue sample or selected area of an organ, or the entirety of an animal, including human, live or not. Means of administration include direct injection into the blood vessel, any means of allowing diffusion of the fluorescent compounds to the tissue or the inner space of the blood vessel, and many means known in the art of targeted delivery using a carrier/recognition device (see, for definition and examples, Tiwari, G. et. al., Int. J. Pharm. Investig. 2012, 2(1), 2-11; Koren, E. and Torchilin, V., IUBMB Life 2011, 63(8), 586-595). The interaction between the fluorescent compounds and blood vessels/serum can be dissolution of the compounds in blood serum, or attachment/binding of the fluorescent compounds to an object associated with the blood vessel system. The said object includes, but is not limited to a biological macromolecule (such as nucleic acids, proteins, peptides, lipids, polysaccharides et. al.), a vesicle or structural component of a cell, a tissue, and any extended system containing any combinations of the above. The consequence of such interactions is that the blood vessels will become visible when the fluorescent compounds are caused to emit fluorescence, for example, by irradiation of light. The fluorescence emission can be visualized, detected and recorded with a camera and/or other imaging devices to transcribe the image of the blood vessel for analysis. A particular advantage of the current invention is that blood cells are not stained by the fluorescent compounds and show up as dark particles in the fluorescence images. In the case with a live test subject, the motion of blood cells can then be measured in a backdrop of fluorescence to reflect the dynamics of blood flow.

In some embodiment of the invention, as demonstrated in Figure III, the fluorescent compounds, either by themselves or the aid of a carrier/recognition device, have specific affinity to certain biological macromolecules, vesicles or structural components of a cell, tissues, or extended systems containing any combinations of the above. The effect of this affinity is such that, when treated with the fluorescent compounds, blood vessels containing these macromolecules, cell vesicles or structural components, tissues, or extended systems fluoresce upon excitation and are distinguished from other tissues in the test subject.

Another embodiment of the invention comprises contacting live zebrafish, wild type or not, at various development stages, with the fluorescent compounds. To achieve the contact, the fluorescent compounds can in general be formulated as a solution, in DMSO for instance, and added to the fish culture. However, to one skilled in the art, it is understood that there can be a number of other treatment methods for achieving contact such as direct injection of the compounds into the blood stream of the fish, and the compounds can also be formulated in any other ways including but not limited to integration into fish feed and attachment to a molecular device (an antibody, other targeting biological macromolecules, a polymer vehicle, an inclusion host such as cyclodextrins, various carbon nano materials et. al.) suitable for these respective treatments. The fluorescent compounds enter the zebrafish vascular system as a result of such treatment, causing the blood vessels to fluoresce upon excitation and the fluorescence image of the blood vessels and the motion of blood flow can be observed with a microscope. The images can also be recorded with an image capturing device such as a camera. As demonstrated in Figure IV, one particular advantage of the current method is that the lethal dosages of the fluorescent compounds of this invention are substantially higher than their working concentrations. The test animals can be examined live throughout the study. Further advantage of the current invention, which is in significant contrast to the transgenic zebrafish models, resides in the fact that the fluorescent compounds are exogenously administered and can be allowed to clear out of the test animals when so desired (see Figure I), such as when further procedures are required with the test animals and the fluorescence may interfere.

In another embodiment of the invention, live zebrafish embryos are exposed to a substance of choice prior to completion of blood vessel formation, under a pre-determined set of conditions appropriate for the interaction between the substance(s) and the fish. After the exposure, the tested zebrafish are put in contact with the fluorescent compounds. Fluorescence images of the zebrafish blood vessels and the motion of blood flow are recorded and analyzed for the effect of the choice substance on blood vessel formation. In general, defective or promiscuous blood vessels resulting from exposure to the choice substances can be readily spotted from the fluorescence images by someone skilled in the art. The extent of abnormality can also be quantified using an image analysis software, such as ImageJ, an open architecture, Java-based image processing program developed at the US National Institute of Health. Within the context of this embodiment, the term "substance" designates any product in isolated form or in mixture with any other material or product(s). The substance may be defined in terms of structure and composition, or it may be undefined. For instance, the substance may be an isolated and structurally-defined product, an isolated product of unknown structure, a mixture of several known and characterized products or an undefined composition comprising one or several products. Examples of such undefined compositions include for instance tissue samples, biological fluids, cell supernatants, vegetal preparations, etc. The candidate substance may be any organic or inorganic product, including a polypeptide (or a protein or peptide), a nucleic acid, a lipid, a polysaccharide, a chemical product, or any mixture or derivatives thereof. The substance may be of natural origin, synthetic origin, including libraries of compounds. This invention is particularly adapted for the screening of large numbers of substances, such as combinatorial libraries of compounds. This invention provides materials and methods allowing efficient and simple screening of several substances in short periods of time. In particular, these methods can be partially automated, thereby allowing efficient and simultaneous screening of large sets of substances. When the activity of the candidate substance(s) is unknown, the method allows the screening or identification of substances exhibiting inhibitory or stimulating activity in terms of blood vessel formation. Alternatively, when the activity (or type of activity) of the candidate substance(s) is known or expected, the method can be used to further characterize said activity (in terms of specificity, efficacy, et. al.) and/or to improve said activity, by assaying derivatives of said candidate substances. An example, with its result in Figure II, is provided to this end with Sunitinib which is a known angiogenesis inhibitor (see Roskoski, R. Jr., Biochem. Biophys. Res. Comm. 2007, 356, 323-328).

DETAILED DESCRIPTION OF THE INVENTION

Figure 1:
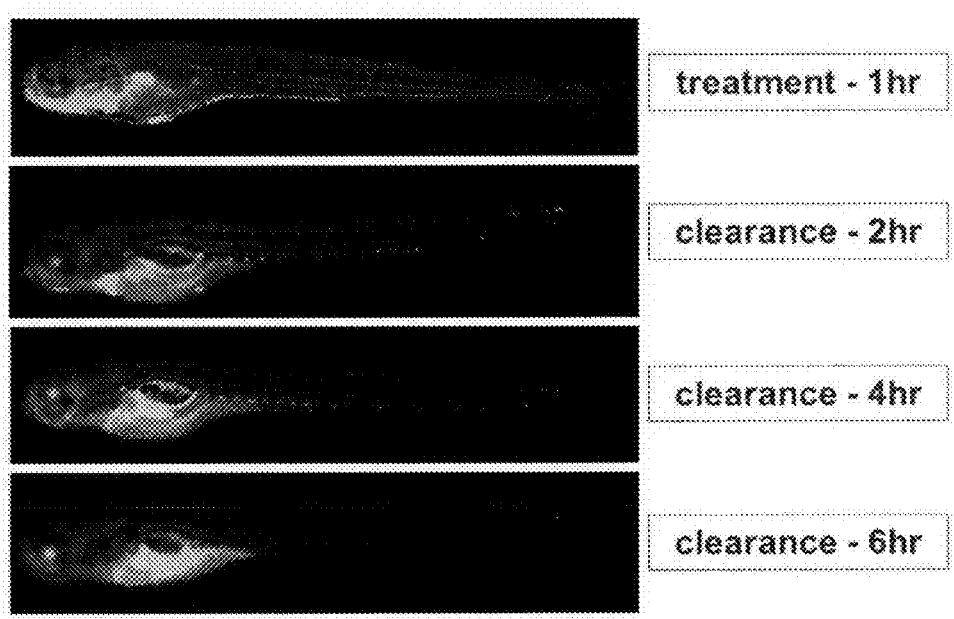
FIG. 1: Fluorescent compounds of this invention are vital and can be systematically cleared by the test animal after administration. After staining with ethyl 4-(3-(6-methoxy-2-oxo-2H-chromen-3-yl)-5-phenyl-4,5-dihydro-1H-pyrazol-1-yl)benzoate (10 µM) for 1 hour, continuous culture of tested zebrafish in RO water allows the dye to clear away. Pictures show incremental fading of green fluorescence over time within the first 6 hours.
Figure 2:
FIG. 2: Confirmation of the anti-angiogenic effect of Sunitinib using the method of this invention. This figure contains microscopic images of zebrafish, treated with Sunitinib followed by staining with 4-(5-(4-(ethoxycarbonyl)phenyl)-3-(6-methoxy-2-oxo-2H-chromen-3-yl)-4,5-dihydro-1H-pyrazol-1-yl)benzoic acid (20 µM), showing increasing deficiency of vascular development upon treatment with higher Sunitinib dose. (a) control; (b) 1 µM Sunitinib; (c) 2.5 µM Sunitinib; (d) 5 µM Sunitinib. Whole fish images were made by combining three segmental images and the scale bar is 100 µm. In each experiment, (a) to (c), four pictures are shown, from top to bottom respectively: bright field whole fish, green fluorescence whole fish, and 2 times magnified images (scale bar is 50 µm) of the inset at two different focus points.
Figure 2:
Figure 2:
Figure 2:
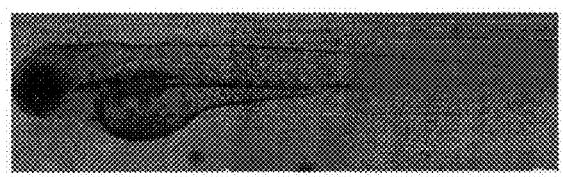
Figure 2:
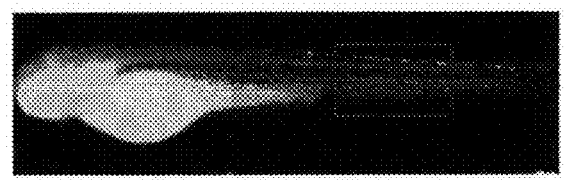
Figure 2:
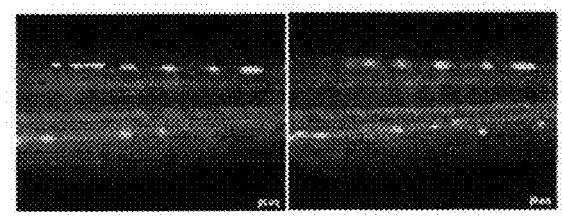
Figure 2:
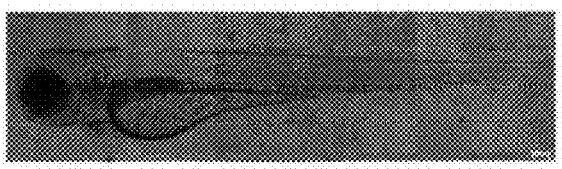
Figure 2:
Figure 2:
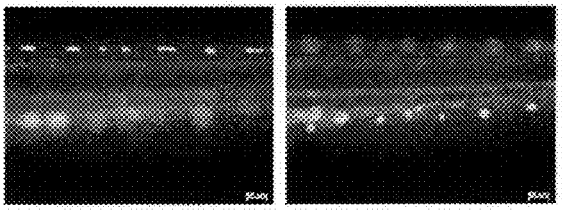
Figure 2:
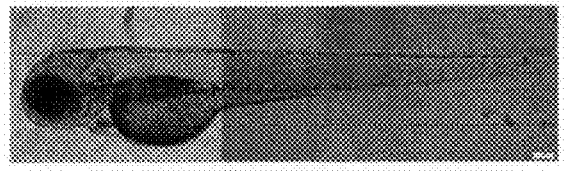
Figure 2:
Figure 2:
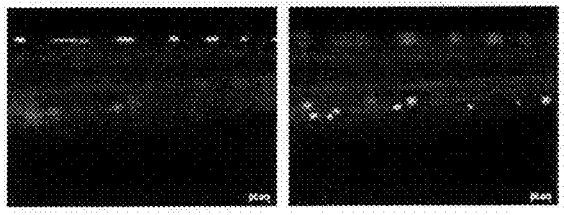
Figure 3:
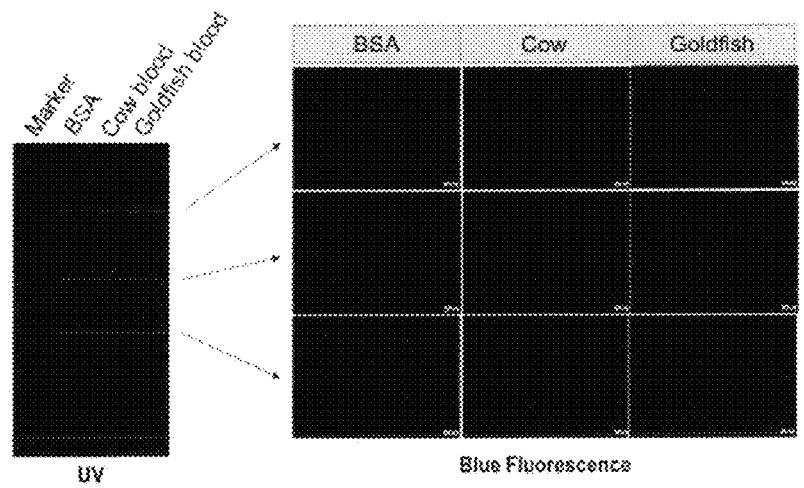
FIG. 3: Fluorescent compounds of this invention display specific binding affinity to certain elements of the vascular system. This figure shows a series of Native PAGE results of BSA, cow blood serum, and goldfish (*Carassius auratus*) blood serum. (a) Before staining with ethyl 1,3-diphenyl-1H-pyrazole-4-carboxylate, visualized with UV (left panel) and fluorescence (right panel, under microscope, approximate position of focus shown by horizontal lines, scale bar is 200 µm), showing no UV or fluorescence. (b) After staining with ethyl 1,3-diphenyl-1H-pyrazole-4-carboxylate (25 µM), visualized with UV (middle panel), fluorescence (right panel, under microscope, approximate position of focus shown by horizontal lines, scale bar is 200 μm), and Coomassie brilliant blue (left panel) in that order, showing UV as well as matching blue fluorescence characteristic of ethyl 1,3-diphenyl-1H-pyrazole-4-carboxylate in both the cow and the fish blood bands.
Figure 3:
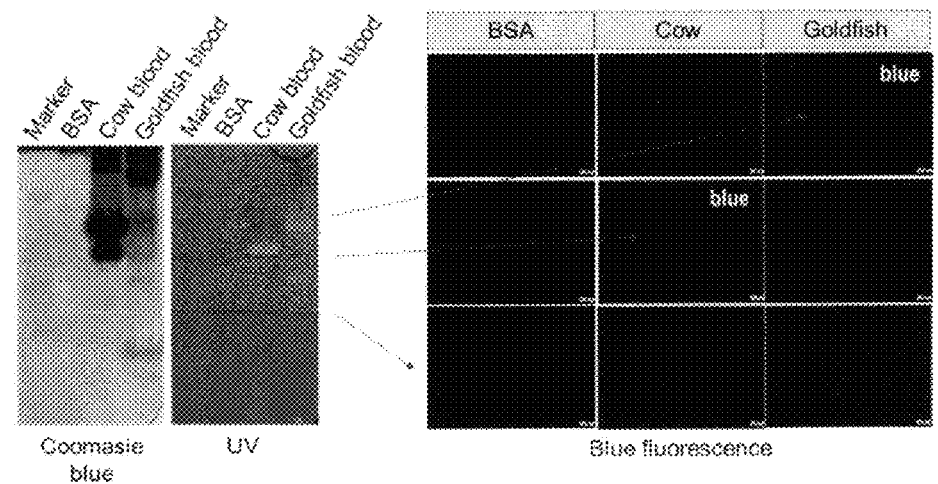
Figure 4:
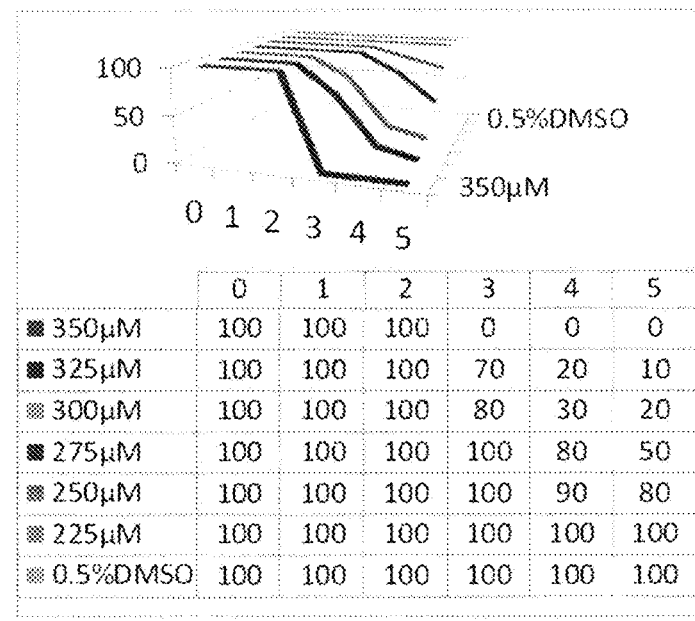
FIG. 4: Acute toxicity of diethyl 4,4'-(3-(6-methoxy-2-oxo-2H-chromen-3-yl)-4,5-dihydro-1H-pyrazole-1,5-diyl) dibenzoate on zebrafish over a five-day regimen. Calculated $LC_{50}$ is 272 μM using the Benchmark Dose Software (BMDS) developed by the US Environmental Protection Agency. Regular working concentration of this compound for staining zebrafish blood vessels is 10-25 μM.
Figure 4:
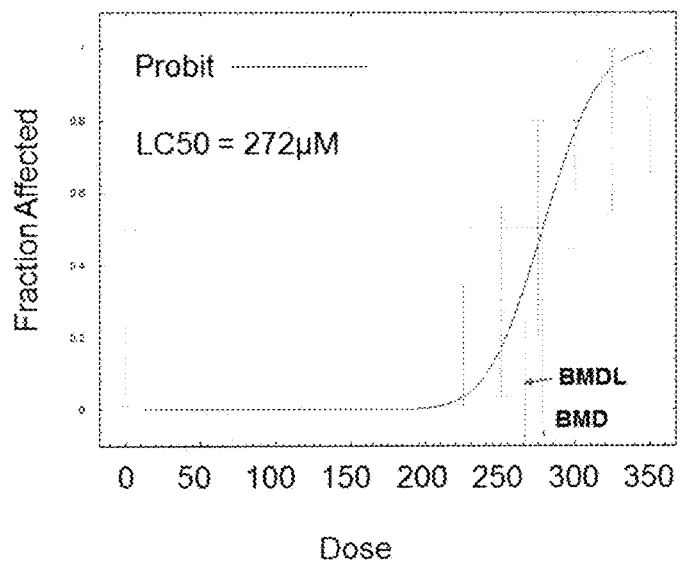

This invention provides a method of visualizing and imaging blood vessels and blood flow in a test subject. The said test subject is either a selected part or the entirety of a dead or living animal, including a human. Detailed steps of implementing this method include: (a) administration of fluorescent compounds described herein and below to the test subject, (b) irradiating the observation area of choice in the test subject with an appropriate light source to excite the administered fluorescent compounds, (c) reveal of blood vessels, or motion of blood flow when appropriate, in the test subject when the fluorescent compounds emit fluorescence, and, (d) observation and recording of the fluorescent images of the blood vessels and blood flow with appropriate devices such as a microscope and a camera.

Fluorescent compounds suitable for the method taught above include compounds of Formula I:

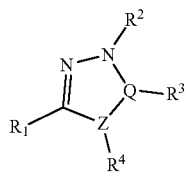

I

Wherein;
$R^1$, $R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;
Q-Z is either C—C, C=C, C—N, C=N, N—C, or N=C; and pharmaceutically acceptable salts, solvates, chelates, non-covalent complexes, prodrugs, mixtures thereof, including both R and S enantiomeric forms and racemic mixtures thereof, as well as a pharmaceutical Formulation containing the compound.

Compounds of Formula I include compounds of Formula IV:

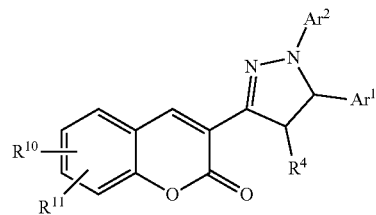

IV

Wherein;
$Ar^1$ and $Ar^2$ are independently selected from aryl or heteroaryl optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;
$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

Specific examples of compounds of Formula IV include:
1) 4-(3-(6-Methoxy-2-oxo-2H-chromen-3-yl)-5-phenyl-4,5-dihydro-1H-pyrazol-1-yl)benzoic acid,
2) 4-(3-(7-(3-Bromopropoxy)-2-oxo-2H-chromen-3-yl)-5-phenyl-4,5-dihydro-1H-pyrazol-1-yl)benzoic acid,
3) (11-((4-(3-(6-Methoxy-2-oxo-2H-chromen-3-yl)-5-phenyl-4,5-dihydro-1H-pyrazol-1-yl)benzoyl)oxy)undecyl) triphenylphosphonium,
4) Ethyl 4-(3-(6-methoxy-2-oxo-2H-chromen-3-yl)-5-phenyl-4,5-dihydro-1H-pyrazol-1-yl)benzoate
5) 5-Chloropentyl 4-(3-(6-methoxy-2-oxo-2H-chromen-3-yl)-5-phenyl-4,5-dihydro-1H-pyrazol-1-yl)benzoate, 6) (3R,4R,5S,6R)-6-(Acetoxymethyl)-3-(4-(3-(6-methoxy-2-oxo-2H-chromen-3-yl)-5-phenyl-4,5-dihydro-1H-pyrazol-1-yl)benzamido)tetrahydro-2H-pyran-2,4,5-triyltriacetate, 7) 4-(3-(6-Methoxy-2-oxo-2H-chromen-3-yl)-1-phenyl-4,5-dihydro-1H-pyrazol-5-yl)benzoic acid, 8) (3-((3-(1-(4-Carboxyphenyl)-5-phenyl-4,5-dihydro-1H-pyrazol-3-yl)-2-oxo-2H-chromen-7-yl)oxy)propyl)triphenylphosphonium, 9) Ethyl 4-(3-(6-methoxy-2-oxo-2H-chromen-3-yl)-1-phenyl-4,5-dihydro-1H-pyrazol-5-yl)benzoate, 10) 2,5-Dioxopyrrolidin-1-yl 4-(3-(6-methoxy-2-oxo-2H-chromen-3-yl)-5-phenyl-4,5-dihydro-1H-pyrazol-1-yl)benzoate, 11) 4-(3-(6-Methoxy-2-oxo-2H-chromen-3-yl)-5-phenyl-4,5-dihydro-1H-pyrazol-1-yl)-N-((3R,4R,5S,6R)-2,4,5-trihydroxy-6-(hydroxymethyl)tetrahydro-2H-pyran-3-yl)benzamide, 12) 3-(1-(4-Fluorophenyl)-5-phenyl-4,5-dihydro-1H-pyrazol-3-yl)-6-methoxy-2H-chromen-2-one, 13) (3-((4-(3-(6-Methoxy-2-oxo-2H-chromen-3-yl)-1-phenyl-4,5-dihydro-1H-pyrazol-5-yl)benzoyl)oxy)propyl)triphenylphosphonium, 14) (Z)-5-((5-Fluoro-2-oxoindolin-3-ylidene)methyl)-N-(2-(4-(3-(6-methoxy-2-oxo-2H-chromen-3-yl)-5-phenyl-4,5-dihydro-1H-pyrazol-1-yl)benzamido)ethyl)-2,4-dimethyl-1H-pyrrole-3-carboxamide, 15) Diethyl 4,4'-(3-(6-methoxy-2-oxo-2H-chromen-3-yl)-4,5-dihydro-1H-pyrazole-1,5-diyl)dibenzoate, 16) 3-(2-(5-(((3aS,4S,6aR)-2-Oxohexahydro-1H-thieno[3,4-d]imidazol-4-yl)pentanoyl)hydrazinyl)propyl 4-(3-(6-methoxy-2-oxo-2H-chromen-3-yl)-5-phenyl-4,5-dihydro-1H-pyrazol-1-yl)benzoate hydrochloride, 17) 3-Bromopropyl 4-(3-(6-methoxy-2-oxo-2H-chromen-3-yl)-1-phenyl-4,5-dihydro-1H-pyrazol-5-yl)benzoate, 18) (Z)-3-((2-(5-((5-Fluoro-2-oxoindolin-3-ylidene)methyl)-2,4-dimethyl-1H-pyrrole-3-carboxamido)ethyl)amino)propyl 4-(3-(6-methoxy-2-oxo-2H-chromen-3-yl)-5-phenyl-4,5-dihydro-1H-pyrazol-1-yl)benzoate hydrochloride, 19) 4-(5-(4-(Ethoxycarbonyl)phenyl)-3-(6-methoxy-2-oxo-2H-chromen-3-yl)-4,5-dihydro-1H-pyrazol-1-yl)benzoic acid, 20) 4-(3-(6-Methoxy-2-oxo-2H-chromen-3-yl)-5-phenyl-4,5-dihydro-1H-pyrazol-1-yl)-N'-(5-((3aS,4S,6aR)-2-oxohexahydro-1H-thieno[3,4-d]imidazol-4-yl)pentanoyl)benzohydrazide, and 21) Ethyl 4-(5-(3,4-dimethoxyphenyl)-3-(6-methoxy-2-oxo-2H-chromen-3-yl)-4,5-dihydro-1H-pyrazol-1-yl)benzoate, and 22) Ethyl 3-(7-hydroxy-2-oxo-2H-chromen-3-yl)-1,5-diphenyl-4,5-dihydro-1H-pyrazole-4-carboxylate.

Compounds of Formula I include compounds of Formula VII:

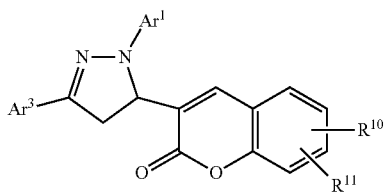

VII

Wherein;
Ar$^1$ and Ar$^3$ are independently selected from aryl or heteroaryl optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

R$^{10}$ and R$^{11}$ are independently selected from hydrogen, halogen, nitro, cyano, OR$^5$, OC(O)R$^5$, NR$^5$R$^6$, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro.

Specific examples of compounds of Formula VII include:

23) Ethyl 4-(5-(7-hydroxy-2-oxo-2H-chromen-3-yl)-3-phenyl-4,5-dihydro-1H-pyrazol-1-yl)benzoate, and 24) Ethyl 4-(5-(7-(3-bromopropoxy)-2-oxo-2H-chromen-3-yl)-3-phenyl-4,5-dihydro-1H-pyrazol-1-yl)benzoate.

Compounds of Formula I include compounds of Formula IX:

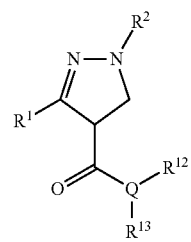

IX

Wherein;
R$^1$ and R$^2$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, halogen, cyano, and nitro;

Wherein R$^5$ and R$^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

Q is independently chosen from nitrogen or oxygen;

$R^{12}$ and $R^{13}$ are independently selected from hydrogen, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

Specific examples of compounds of Formula IX include:
25) N-Benzyl-1,3-diphenyl-4,5-dihydro-1H-pyrazole-4-carboxamide,
26) Ethyl 1-(4-fluorophenyl)-3-phenyl-4,5-dihydro-1H-pyrazole-4-carboxylate, and
27) 4-(4-(Ethoxycarbonyl)-3-phenyl-4,5-dihydro-1H-pyrazol-1-yl)benzoic acid.

Compounds of Formula I include compounds of Formula X:

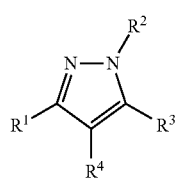

X

Wherein;

$R^1$, $R^2$, $R^3$, and $R^4$ are independently selected from hydrogen, alkyl, substituted saturated or unsaturated alkyl, $S(O)_{1-2}R^5$, $SO_2NR^5R^6$, $C(O)R^5$, $C(O)OR^5$, and $C(O)NR^5R^6$; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro.

Compounds of Formula X include compounds of Formula XIII:

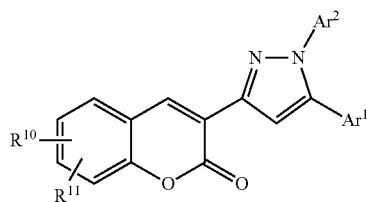

XIII

Wherein;

$Ar^1$ and $Ar^2$ are independently selected from aryl or heteroaryl optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro.

Specific examples of compounds of Formula XIII include:
28) Ethyl 4-(3-(6-methoxy-2-oxo-2H-chromen-3-yl)-1-phenyl-1H-pyrazol-5-yl)benzoate,
29) 3-(5-(3,4-Dimethoxyphenyl)-1-phenyl-1H-pyrazol-3-yl)-6-methoxy-2H-chromen-2-one, and
30) 4-(5-([1,1'-Biphenyl]-4-yl)-3-(6-methoxy-2-oxo-2H-chromen-3-yl)-1H-pyrazol-1-yl)benzoic acid.

Compounds of Formula X include compounds of Formula XV:

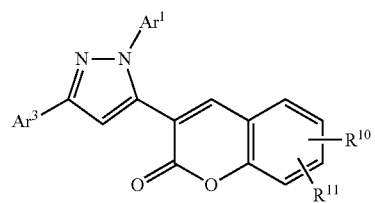

XV

Wherein;

$Ar^1$ and $Ar^3$ are independently selected from aryl or heteroaryl optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

$R^{10}$ and $R^{11}$ are independently selected from hydrogen, halogen, nitro, cyano, $OR^5$, $OC(O)R^5$, $NR^5R^6$, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

Specific examples of compounds of Formula XV include:
31) Ethyl 4-(5-(7-hydroxy-2-oxo-2H-chromen-3-yl)-3-phenyl-1H-pyrazol-1-yl)benzoate.

Compounds of Formula X include compounds of Formula XVII:

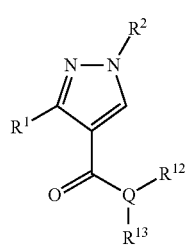

XVII

Wherein;

$R^1$ and $R^2$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, $R^5P(R^6)_3$, halogen, cyano, and nitro;

Q is independently chosen from nitrogen or oxygen;

$R^{12}$ and $R^{13}$ are independently selected from hydrogen, alkyl, optionally substituted saturated or unsaturated alkyl, a substituted or unsubstituted aryl; $S(O)_{1-2}R^5$, $SO_2NR^5R^6$, $C(O)R^5$, $C(O)OR^5$, and $C(O)NR^5R^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^5$, $C(O)OR^5$, $C(O)NR^5R^6$, $NR^5C(O)R^6$, $NR^5C(O)OR^6$, $R^5P(R^6)_3$, halogen, cyano, and nitro.

Specific examples of compounds of Formula XVII include:
32) Ethyl 1,3-diphenyl-1H-pyrazole-4-carboxylate,
33) 5-((1,3-Diphenyl-1H-pyrazole-4-carboxamido)methyl)-1-ethyl-2-((1E,3E)-3-(1-ethyl-3,3-dimethylindolin-2-ylidene)prop-1-en-1-yl)-3,3-dimethyl-3H-indol-1-ium,
34) Ethyl 1-(4-fluorophenyl)-3-phenyl-1H-pyrazole-4-carboxylate, and
35) N-Benzyl-1-(4-fluorophenyl)-3-phenyl-1H-pyrazole-4-carboxamide.

Compounds of Formula X include compounds of Formula XVIII:

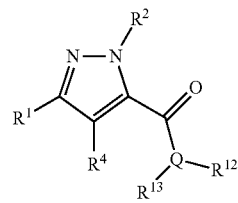

XVIII

Wherein;

$R^1$, $R^2$, and $R^4$ are independently selected from hydrogen, alkyl, substituted saturated or unsaturated alkyl; an unsubstituted or substituted aryl, and an unsubstituted or substituted, aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, $NR^5SO_2R^6$, $C(O)R^6$, $C(O)OR^5$, $C(O)NR^5R^6$, $NR^5C(O)R^6$, $NR^5C(O)OR^6$, halogen, cyano, and nitro;

Wherein $R^5$ and $R^6$ are independently chosen from hydrogen, an optionally substituted saturated or unsaturated alkyl; and an unsubstituted or substituted cycloalkyl, an unsubstituted or substituted 8-12 bicyclic membered ring, an unsubstituted or substituted aryl, heterocycloalkyl, or heteroaryl group having 1-4 heteroatoms independently selected from nitrogen, oxygen, or sulfur, optionally substituted with 1-6 substituents independently selected from the group consisting of OH, $R^5$, $OR^5$, $OC(O)R^5$, $NR^5R^6$, $S(O)_{1-2}R^5$, $SO_2NR^5R^6$, NR$^5$SO$_2$R$^6$, C(O)R$^6$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro;

Q is independently chosen from nitrogen or oxygen;

R$^{12}$ and R$^{13}$ are independently selected from hydrogen, alkyl, optionally substituted saturated or unsaturated alkyl, a substituted or unsubstituted aryl; S(O)$_{1-2}$R$^5$, SO$_2$NR$^5$R$^6$, C(O)R$^5$, C(O)OR$^5$, and C(O)NR$^5$R$^6$; and an aromatic or non-aromatic, 3-8 membered monocyclic ring, or 8-12 bicyclic membered ring, having 0-4 heteroatoms independently selected from nitrogen, oxygen, or sulfur, optionally substituted with 1-6 substituents independently selected from the group consisting of OH, R$^5$, OR$^5$, OC(O)R$^5$, NR$^5$R$^6$, S(O)$_{1-2}$R$^5$, SO$_2$NR$^5$R$^6$, NR$^5$SO$_2$R$^6$, C(O)R$^5$, C(O)OR$^5$, C(O)NR$^5$R$^6$, NR$^5$C(O)R$^6$, NR$^5$C(O)OR$^6$, R$^5$P(R$^6$)$_3$, halogen, cyano, and nitro.

Specific examples of compounds of Formula XVIII include:

36) 4-Chloro-6-(4-(4-methoxyphenyl)-5-methyl-1H-pyrazol-3-yl)benzene-1,3-diol,
37) 3-(5-Chloro-2,4-dihydroxyphenyl)-4-(4-methoxyphenyl)-1H-pyrazole-5-carboxylic acid,
38) 3-(5-Chloro-2,4-dihydroxyphenyl)-4-(4-methoxyphenyl)-N-phenyl-1H-pyrazole-5-carboxamide,
39) 3-(5-Chloro-2,4-dihydroxyphenyl)-N-(3-((3-(3-fluorophenyl)-2-oxo-2H-chromen-7-yl)oxy)propyl)-4-(4-methoxyphenyl)-1H-pyrazole-5-carboxamide,
40) 5-((3-(5-Chloro-2,4-dihydroxyphenyl)-4-(4-methoxyphenyl)-1H-pyrazole-5-carboxamido)methyl)-1-ethyl-2-((1E,3E)-3-(1-ethyl-3,3-dimethylindolin-2-ylidene)prop-1-en-1-yl)-3,3-dimethyl-3H-indol-1-ium,
41) Ethyl 1-(4-(benzylcarbamoyl)phenyl)-3-phenyl-4,5-dihydro-1H-pyrazole-4-carboxylate, and
42) Sodium 1-(4-(benzylcarbamoyl)phenyl)-3-phenyl-4,5-dihydro-1H-pyrazole-4-carboxylate.

The said method of visualizing and imaging blood vessels and blood flow of this invention includes a method wherein the test subject is zebrafish (*Danio rerio*).

This invention further provides a method to identify, select, characterize, or collectively screen for substances that inhibit or promote blood vessel formation or angiogenesis in living, wild type or genetically altered zebrafish. Detailed procedure of implementing this method of screening starts with exposing test zebrafish to selected substance or mixture of substances under a pre-determined set of conditions appropriate for the interaction between the substance(s) and the fish. The fish is then subjected to the said method of visualizing and imaging blood vessels and blood flow of this invention. The resulting images of blood vessels and blood flow are examined to determine the extent of effect on zebrafish blood vessel formation, or angiogenesis, caused by the selected substance(s).

Definitions

Unless noted otherwise, the chemical, biological, pharmacological, and other technical terms used herein are consistent with the uses of these terms in contemporary technical journals, patents, textbooks, and other references devoted to the appropriate art. For example, definitions and explanations of organic chemistry terms may be found in standard text such as the latest edition of March's Advanced Organic Chemistry, John Wiley & Sons, Inc, New York. (e.g. 5th Ed., 2001). In the interest of clarity and the convenience of the reader, the definitions of some terms frequently used herein are listed below.

"Alkyl" refers to a branched or straight chain hydrocarbon group containing from one to 16 carbon atoms derived by the removal of one hydrogen atom from a single carbon atom of a parent alkane, alkene or alkyne group. The term "saturated alkyl" is intended to include groups having exclusively single carbon-carbon bonds. The term "unsaturated alkyl" is specifically intended to include groups having any degree or level of unsaturation, i.e., groups having one or more double carbon-carbon bonds, groups having one or more triple carbon-carbon bonds and groups having mixtures of single, double and triple carbon-carbon bonds.

The terms "halo" and "halogen" as used herein to identify substituent moieties, represent fluorine, chlorine, bromine or iodine, preferably chlorine or fluorine.

The term "alkoxy" as used alone or in combination herein refers to a straight or branched chain alkyl group covalently bonded to the parent molecule through an —O-linkage containing from one to 22 carbon atoms.

The term "alkoxyalkyl" refers to an alkyl group substituted with an alkoxy group.

The term "haloalkyl" is a substituted alkyl, preferably a substituted lower alkyl, substituted with one or more halogen atoms, and preferably is a $C_1$ to $C_4$ alkyl substituted with one to three halogen atoms.

The term "alkanoyl" as used alone or in combination herein refers to an acyl radical derived from an alkanecarboxylic acid.

The term "aminocarbonyl" means an amino-substituted carbonyl (carbamoyl or carboxamide) wherein the amino group can be a primary, secondary (mono-substituted amino) or tertiary amino (di-substituted amino) group.

The term "cycloalkyl" refers to stable, saturated or partially unsaturated monocyclic, bridged monocyclic, bicyclic, and spiro rings of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. The term "optionally substituted" as it refers to "cycloalkyl" herein indicates that the cycloalkyl group may be substituted at one or more substitutable ring positions by one or more groups independently selected from alkyl, hydroxy, alkoxy, nitro, monoalkylamino, dialkylamino, cyano, halo, haloalkyl, alkanoyl, am inocarbonyl, monoalkylaminocarbonyl, dialkylaminocarbonyl, alkyl amido, alkoxyalkyl, alkoxycarbonyl, alkylcarbonyloxy and aryl and optionally substituted aryl. A cycloalkyl group can have one or more carbon-carbon double or triple bonds in the ring so long as the ring is not rendered aromatic by their presence. The term "saturated cycloalkyl" is intended to include cyclic rings having exclusively single carbon-carbon bonds. The term "unsaturated cycloalkyl" is specifically intended to include cyclic rings having any degree or level of unsaturation, i.e., groups having one or more double carbon-carbon bonds, groups having one or more triple carbon-carbon bonds and groups having mixtures of single, double and triple carbon-carbon bonds.

"Bicyclic" includes spirocyclic, ortho-fused and bridged bicyclic systems. "Spirocyclic" refers to a pair of rings having a single atom in common. "Ortho-fused" refers to a pair of rings having two adjacent atoms in common. "Bridged bicyclic" refers to a pair of rings having at least three adjacent atoms in common.

The term "heterocycloalkyl" as used herein refers to a stable, saturated, or partially unsaturated, monocyclic, bridged monocyclic, bicyclic, and spiro ring system containing carbon atoms and other atoms selected from nitrogen, sulfur and/or oxygen. Preferably, a heterocycloalkyl is a 5 or 6-membered monocyclic ring or an 8-12 membered bicyclic ring which consists of carbon atoms and contains one, two, or three heteroatoms selected from nitrogen, oxygen and/or sulfur. The term "optionally substituted" as it refers to "heterocycloalkyl" herein indicates that the heterocycloalkyl group may be substituted at one or more substitutable ring positions by one or more groups independently selected from alkyl, alkoxy, nitro, monoalkylamino, dialkylamino, cyano, halo, haloalkyl, alkanoyl, aminocarbonyl, monoalkylaminocarbonyl, dialkylaminocarbonyl, alkyl amido, alkoxyalkyl, alkoxycarbonyl, alkylcarbonyloxy and aryl, said aryl being optionally substituted by halo, alkyl, alkoxy, nitro, cyano, haloalkyl, alkanoyl, aminocarbonyl, monoalkylaminocarbonyl, dialkylaminocarbonyl, alkyl amido, alkoxyalkyl, alkoxycarbonyl, and alkylcarbonyloxy groups. The heterocycloalkyl group may be attached to the parent structure through a carbon atom or through any heteroatom of the heterocycloalkyl that results in a stable structure. A heterocycloalkyl group can have one or more carbon-carbon double bonds or carbon-carbon triple bonds, or carbon-heteroatoms double bonds in the ring as long as the ring is not rendered aromatic by their presence. The term "saturated heterocycloalkyl" is intended to include heterocyclic rings having exclusively single bonds in the ring. The term "unsaturated heterocycloalkyl" is specifically intended to include heterocyclic rings having any degree or level of unsaturation, i.e., groups having one or more double bonds, groups having one or more triple bonds and groups having mixtures of single, double and triple bonds.

The term "heteroaryl" as used herein refers to a stable, aromatic monocyclic or bicyclic ring system containing carbon atoms and other atoms selected from nitrogen, sulfur and/or oxygen. Preferably, a heteroaryl is a 5 or 6-membered monocyclic ring or an 8-12 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl, alkoxy, nitro, monoalkylamino, dialkylamino, cyano, halo, haloalkyl, alkanoyl, aminocarbonyl, monoalkylaminocarbonyl, dialkylaminocarbonyl, alkyl amido, alkoxyalkyl, alkoxycarbonyl, alkylcarbonyloxy and aryl, said aryl being optionally substituted by halo, alkyl and alkoxy groups. Examples of such heteroaryl groups are isoxazolyl, imidazolyl, thiazolyl, isothiazolyl, pyridyl, furyl, pyrimidinyl, pyrazolyl, pyridazinyl, furazanyl and thienyl. The heteroaryl group may be attached to the parent structure through a carbon atom or through any heteroatom of the heteroaryl that results in a stable structure.

The term "aryl" when used alone or in combination refers to an unsubstituted or optionally substituted monocyclic, bicyclic or tricyclic aromatic hydrocarbon ring systems. Preferred are optionally substituted phenyl or naphthyl groups. The aryl group may optionally be substituted at one or more substitutable ring positions by one or more groups independently selected from alkyl, alkoxy, nitro, monoalkylamino, dialkylamino, cyano, halo, haloalkyl, alkanoyl, aminocarbonyl, monoalkylaminocarbonyl, dialkylaminocarbonyl, alkyl amido, alkoxyalkyl, alkoxycarbonyl, alkylcarbonyloxy and aryl, said aryl being optionally substituted by halo, alkyl and alkoxy groups. Preferably, the aryl group is phenyl optionally substituted with up to five and usually with one or two groups.

Unless otherwise defined, the term "optionally substituted" as used herein, refers to the substitution of a ring system at one or more positions with one or more groups selected from: $C_{1-24}$ alkyl, $C_{1-24}$ alkoxy, an optionally substituted phenyl, cyano, halo, $C_{1-24}$ alkoxycarbonyl, $C_{1-24}$ alkyl carbonyloxy, mono- & bis-($C_{1-24}$ alkyl)-carboxamide, $C_{1-24}$ alkyl amido, nitro, and mono- & bis-($C_{1-24}$ alkyl)-amino.

"Chelate" refers to the chemical entity formed by the coordination of a compound to a metal ion at two (or more) points.

"Disease" refers to any disease, disorder, condition, symptom, or indication that is not a normal body function.

"Optionally" means that the subsequently described event or circumstance may or may not occur, and that the description includes instances where the event or circumstance occurs and instances in which the event does not.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable excipient, carrier or adjuvant" refers to an excipient, carrier or adjuvant that can be administered to a subject, together with at least one chemical entity of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient or carrier.

"Pharmaceutical formulation," or synonymously "medicament," means a composition containing one or more pharmaceutically active compounds, e.g. one or more chemical entities of the present disclosure, and one or more pharmaceutically acceptable vehicles.

"Prodrug" refers to a derivative of a therapeutically effective compound that requires a transformation within the body to produce the therapeutically effective compound.

"Protecting group" refers to a compound that when introduced into a molecule by chemical modification of a functional group reduces or prevents that reactivity. A list of protecting groups can be found in Green et. al., "Protective Groups in Organic Chemistry," (Wiley and Sons, 4th ed. 2006).

The term "salt" refers to a salt of a compound that is pharmaceutically acceptable and that possesses the desired pharmacological activity of the parent compound. Such salts include but are not limited to: salts formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, and the like. It is possible that a salt that is not pharmaceutically acceptable may be used as a chemical intermediate, but those situations will be note when and where they occur in these teachings.

"Solvate" refers to the compound formed by the interaction of a solvent and a compound. Suitable solvates are pharmaceutically acceptable solvates, such as hydrates, including monohydrates and hemi-hydrates.

"Stereoisomer" refers to an isomer that differs in the arrangement of the constituent atoms in space. Stereoisomers that are mirror images of each other and optically active are termed "enantiomers," and stereoisomers that are not mirror images of one another are termed "diastereoisomers." A mixture of equal amounts of the two stereoisomers of an optically active substance, such as two enantiomers where such a mixture does not rotate plane-polarized light refers to as "racemic mixture".

"Subject" includes mammals, such as humans. The terms "patient," "human," and "subject" are used interchangeably and synonymously herein.

"Substituted" refers to a molecule in which one or more hydrogen atoms are replaced with one or more non-hydrogen atoms, functional groups or moieties.

General Synthetic Procedures:

Chemical entities of the present disclosure can be prepared by methods well known in the art from readily available starting materials using the following general methods and procedures. The skilled artisan will appreciate that where typical or preferred process conditions, such as, reaction temperatures, times, mole ratios of reactants, solvents, pressures, are given, other process conditions can also be used unless otherwise stated. Reaction conditions may vary with the reactants or solvent used, but such conditions can be determined by one skilled in the art by routine optimization procedures.

Furthermore, chemical entities of the present disclosure can contain one or more chiral centers. Accordingly, if desired, such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure, unless otherwise indicated. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

Additionally, as will be apparent to those skilled in the art, conventional protecting groups may be necessary to prevent certain functional groups from undergoing undesired reactions. Suitable protecting groups for various functional groups as well as suitable reaction conditions for protection and deprotection of certain functional groups are well known in the art. For example, the protecting groups which are described in T. W. Greene and P. G. Wuts, Protecting Groups in Organic Synthesis, Third Edition, Wiley, New York, 1999, and references cited therein.

Chemical entities of the present disclosure can be isolated and purified by techniques well known in the art, such as extraction, evaporation, distillation, trituration, chromatography, and recrystallization. General synthetic schemes to prepare the compounds of the present disclosure are presented in the reaction schemes provided herein.

A compound of Formula III can in general be prepared using the teaching in Scheme 1 ($R^4$=—C(O)OEt). See, for reviews on the synthesis of coumarin, Hepworth, J. et. al., in Comprehensive Heterocyclic Chemistry, Pergamon Press, 2nd edition, 1996; Vekariya, R. and Patel, H.; Synth. Comm., 2014, 44(19), 2756-2788. A General method for the synthesis of substituted pyrazolines can be found in Sharma, S. et. al.; Chem. Sci. Trans., 2014, 3(3), 861-875, and references cited therein.

Preparation of coumarin ketoester 3 can be achieved by treating an appropriately substituted aldehyde/ketone 1 with diethyl 3-oxopentanedioate 2 under Knoevenagel condensation reaction conditions. Treatment of intermediate 3 with aldehyde 4, followed by cyclization with hydrazine 6 can afford pyrazoline-coumarin compounds 7. Certain starting materials 1, 4 and 6 are commercially available or can be prepared by methods of the art.

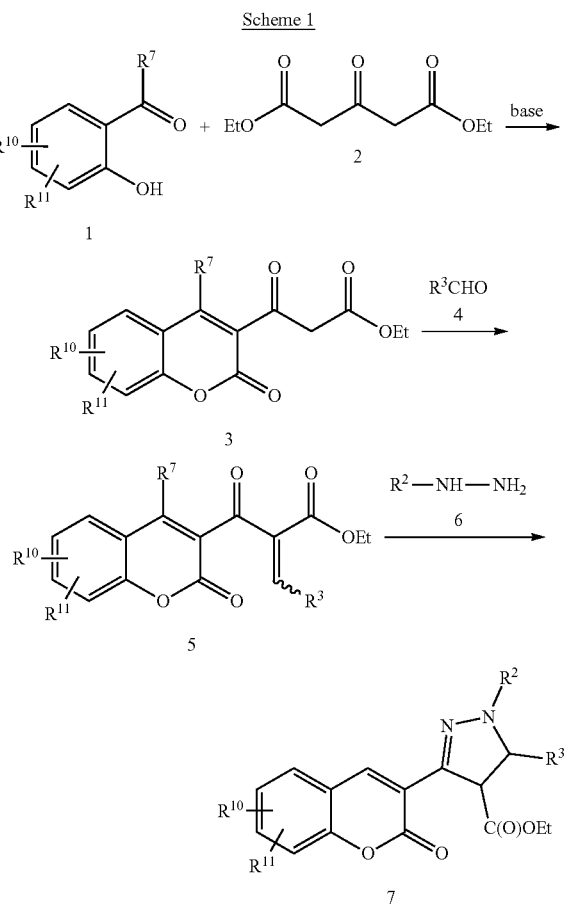

A compound of Formula IV can be prepared as illustrated in Scheme 2. Preparation of substituted coumarin intermediates 10 can be achieved by treating an appropriately substituted coumarin-ketone 8 with a substituted aldehyde 9 under aldol condensation reaction conditions. Treatment of intermediate 10 with a substituted hydrazine 11 under cyclization reaction conditions can afford pyrazoline-coumarin compounds 12. Certain starting materials 8, 9 and 11 are commercially available or can be prepared by methods of the art.

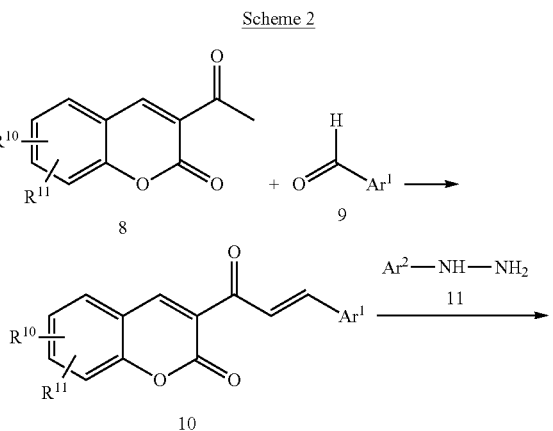

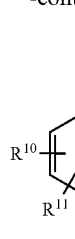

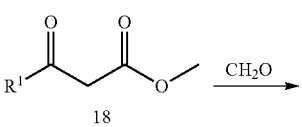

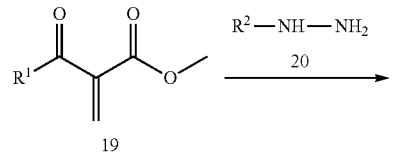

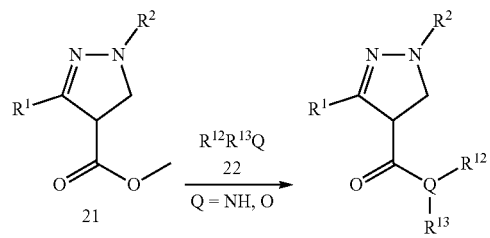

A compound of Formula VII can be prepared as illustrated in Scheme 3. Treatment of a substituted coumarin-aldehyde 13 with a substituted ketone 14 can provide the corresponding unsaturated coumarin-ketone compound 15. Preparation of pyrazoline substituted compounds 17 can be achieved by treating 15 with substituted hydrazines 16 under cyclization reaction conditions. Certain starting materials 13, 14 and 16 are commercially available or can be prepared by methods known to those skilled in the art.

Scheme 3

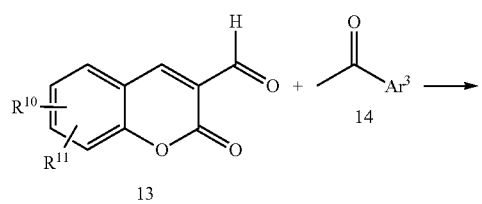

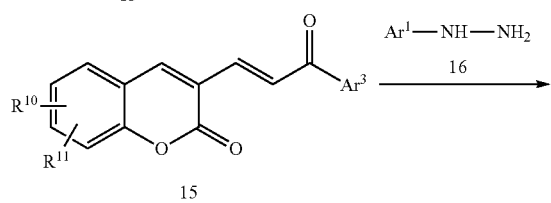

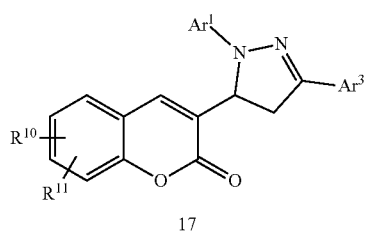

A compound of Formula IX can be prepared as illustrated in Scheme 4. Treatment of a substituted keto-ester 18 with formaldehyde can provide the corresponding unsaturated keto-ester compound 19. Preparation of pyrazoline substituted compounds 21 can be achieved by treating 19 with substituted hydrazines 20 under cyclization reaction conditions to provide the corresponding substituted pyrazoline derivatives 21. Amidation or transesterification of compound 21 can provide the final pyrazoline derivatives 23. Certain starting materials 18, 20 and 22 are commercially available or can be prepared by methods known to those skilled in the art.

A compound of Formula XIII can be prepared as illustrated in Scheme 5. Pyrazoles can in general be synthesized by the oxidation of pyrazolines. See, for examples, Bapat, J. et. al.; Aust. J. Chem., 1972, 25, 1321-3; Nakamichi, N. et. al.; Org. Lett., 2002, 4 (22), 3955-3957, and references cited therein.

Treatment of a substituted coumarin-ketone 8 with an aldehyde 9 under aldol condensation reaction conditions can provide the corresponding unsaturated coumarin derivative 10. Preparation of pyrazoline substituted compounds 12 can be achieved by treating a coumarin-ketone 10 with a substituted hydrazine compound 11 under cyclization reaction conditions to provide the corresponding intermediate 12. Oxidation of 12 can provide the substituted pyrazole compounds 24. Certain starting materials 8, 9 and 11 are commercially available or can be prepared by methods known to those skilled in the art.

Scheme 5

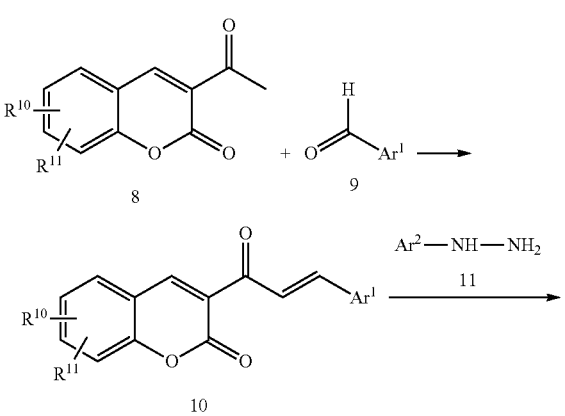

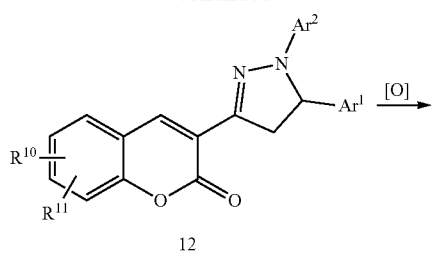

12

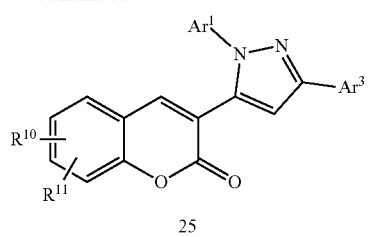

25

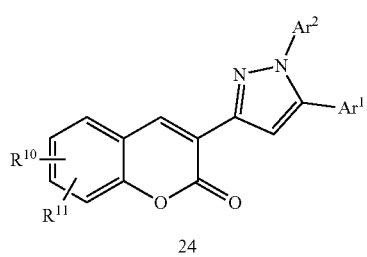

24

A compound of Formula XV can be prepared as illustrated in Scheme 6. Treatment of a substituted coumarin-aldehyde 13 with a substituted ketone 14 can provide the corresponding unsaturated coumarin-ketone compound 15. Preparation of pyrazoline substituted intermediates 17 can be achieved by treating an appropriately substituted compound 15 with substituted hydrazines 16 under cyclization reaction conditions to provide the corresponding final pyrazoline derivative 17. Oxidation of 17 can provide the pyrazole compounds 25. Certain starting materials 13, 14 and 16 are commercially available or can be prepared by methods known to those skilled in the art.

A compound of Formula XVII can be prepared as illustrated in Scheme 7. A general methodology can be found in Crosscurt, A. et. al.; J. Agric. Food Chem., 1979, 27(2), 406-409, and references therein. Treatment of a substituted keto-ester 18 with formaldehyde can provide the corresponding unsaturated keto-ester compound 19. Preparation of pyrazoline substituted compounds 21 can be achieved by treating 19 with substituted hydrazines 20 under cyclization reaction conditions to provide the corresponding substituted pyrazoline derivatives 21. Amidation or transesterification of compound 21 can provide the pyrazoline derivatives 23. Oxidation of 23 can provide pyrazole derivatives 26. Certain starting materials 18, 20 and 22 are commercially available or can be prepared by methods known to those skilled in the art.

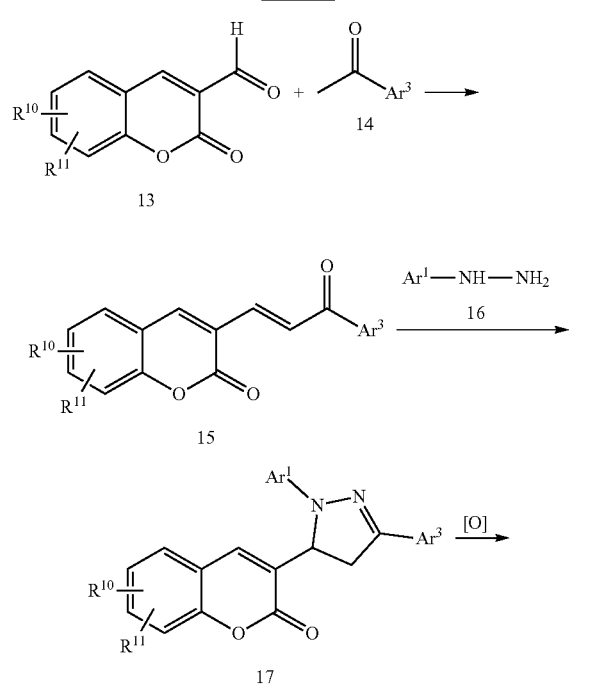

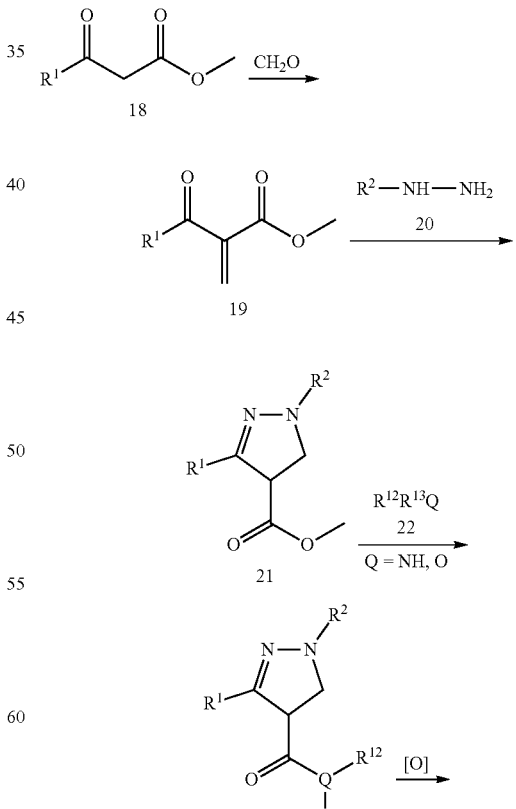

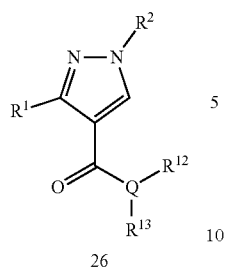

26

A compound of Formula XVIII can be prepared as illustrated in Scheme 8. Treatment of a substituted phenolic compound 27 with a substituted acetic acid 28 can provide the corresponding ketone derivative 29, which after cyclization with a derivative of oxalic acid the corresponding cyclized material 30 can be prepared. Preparation of the pyrazole substituted compounds 31 can be achieved by treating 30 with hydrazine under cyclization reaction conditions to provide the corresponding substituted pyrazole derivatives 31. Amidation or transesterification of compounds 31 can provide the pyrazole derivatives 33. Certain starting materials 27, 28 and 32 are commercially available or can be prepared by methods known to those skilled in the art.

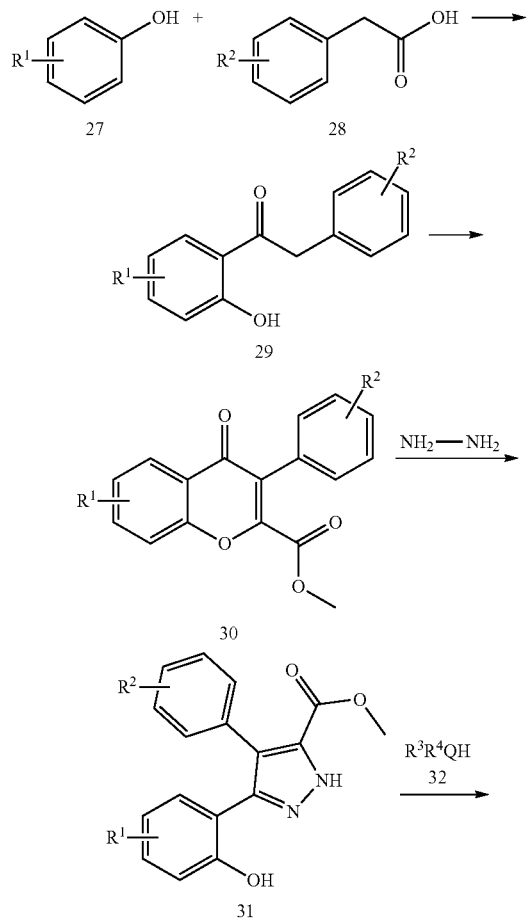

Scheme 8

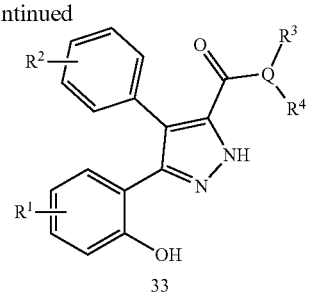

33

EXAMPLES

Example 1 (Formula IV)

Synthesis of 4-(3-(6-methoxy-2-oxo-2H-chromen-3-yl)-5-phenyl-4,5-dihydro-1H-pyrazol-1-yl)benzoic acid

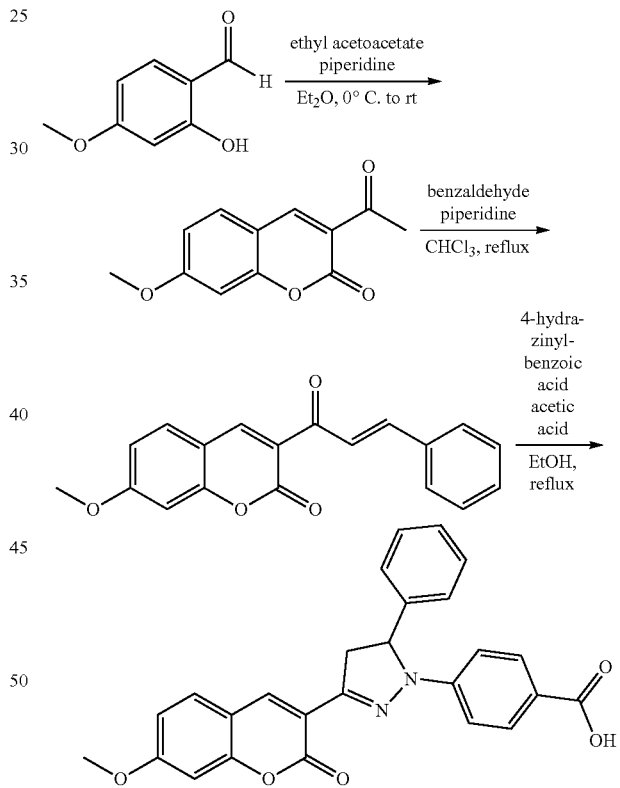

3-Acetyl-6-methoxy-2H-chromen-2-one

To a stirred solution of ethyl acetoacetate (750 mg, 5 mmol) in ethyl ether (10 mL) at 0° C. was added piperidine (250 mg, 3 mmol). 2-Hydroxy-5-methoxybenzaldehyde (750 mg, 5 mmol) was then added dropwise. The mixture was stirred for 20 min. at 0° C., followed by overnight at room temperature. The resultant yellow suspension was filtered. The solid was washed with ether and dried to give 3-acetyl-6-methoxy-2H-chromen-2-one as a yellow powder (950 mg, 82%).

3-Cinnamoyl-7-methoxy-2H-chromen-2-one

To a 2-neck RB flask equipped with a condenser under nitrogen were added 3-acetyl-7-methoxy-2H-chromen-2-one (200 mg, 0.9 mmol), benzaldehyde (120 mg, 1.2 mmol), piperidine (20 mg, 0.18 mmol) and chloroform (3 mL). The mixture was stirred under reflux for 48 hrs, cooled to rt and cold methanol (2 mL) was added with stirring. The solid was collected, washed with ether and dried under vacuum to give yellow powder. Yield: 180 mg, 61%.

4-(3-(6-methoxy-2-oxo-2H-chromen-3-yl)-5-phenyl-4,5-dihydro-1H-pyrazol-1-yl)benzoic acid To a 2-neck RB flask equipped with a condenser under nitrogen were added 3-cinnamoyl-7-methoxy-2H-chromen-2-one (100 mg, 0.32 mmol), 4-hydrazinylbenzoic acid (60 mg, 0.39 mmol), acetic acid (0.25 mL, 4.16 mmol) and ethanol (20 mL). The mixture was stirred under reflux overnight and then cooled to rt. Water (10 mL) was added over 10 minutes with stirring. The solid was collected, washed with cold ethanol and ether and dried under vacuum to give orange solid. Yield: 52 mg, 36%.

Example 2 (Formula IV)

Synthesis of ethyl 3-(7-hydroxy-2-oxo-2H-chromen-3-yl)-1,5-diphenyl-4,5-dihydro-1H-pyrazole-4-carboxylate

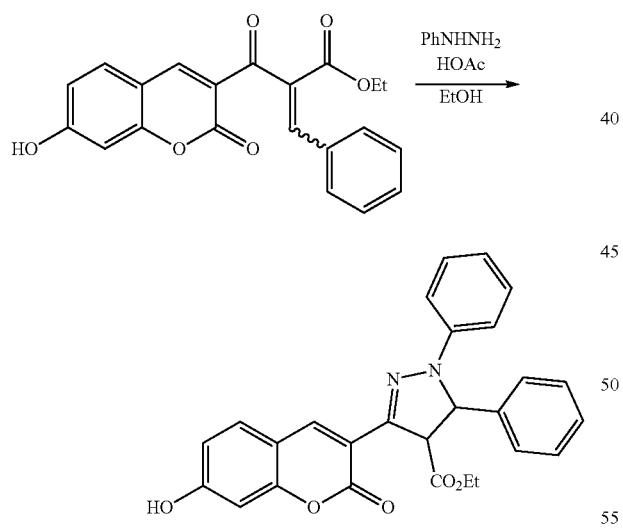

Ethyl 2-(7-hydroxy-2-oxo-2H-chromene-3-carbonyl)-3-phenylacrylate (80 mg, 0.22 mmol, see, for preparation, Vitorio, F. et. al. New J. Chem., 2015, 39, 2323-2332), phenylhydrazine (25 g, 0.23 mmol), acetic acid (0.1 mL) and ethanol (1 mL) were placed in a 5 mL pressured flask. The reaction mixture was heated in an oil bath at 100° C. for 10 hours. The solvent was removed under reduced pressure and the residue was purified by column chromatography (EtOAc/hexane=2:1). Yield: 36%.

Example 3 (Formula VII)

Synthesis of ethyl 4-(5-(7-hydroxy-2-oxo-2H-chromen-3-yl)-3-phenyl-4,5-dihydro-1H-pyrazol-1-yl)benzoate

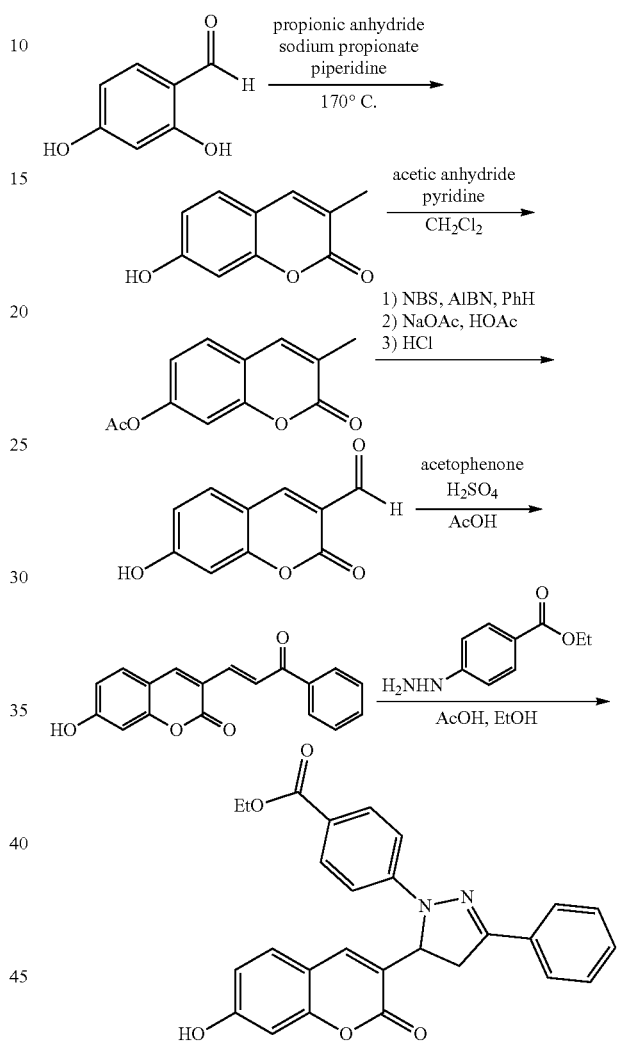

7-Hydroxy-3-methyl-2H-chromen-2-one

To a 10 mL RB flask was added 2,4-dihydroxybenzaldehyde (1 g), sodium propionate (1.5 g), piperidine (0.1 mL) and propionic anhydride (2.5 mL). The mixture was heated to 170° C., poured into ice water, and 1N HCl was added to bring the pH to ca. 3. The solid was collected by filtration, mixed with 1 mL of sulfuric acid, and poured into ice water. The solid was collected, washed with H₂O and ether, and dried under vacuum. Yield: 85%.

3-Methyl-2-oxo-2H-chromen-7-ylacetate

To a 2-neck RB flask were added 7-hydroxy-3-methyl-2H-chromen-2-one (759 mg, 0.34 mmol), acetic acid (2 mL), pyridine (0.07 mL) and dichloromethane (14 mL). The mixture was stirred at rt overnight and then evaporated under reduced pressure. The residue was purified by chromatography (eluted with EtOAc/hexane=1:1). Yield: 72%.

7-Hydroxy-2-oxo-2H-chromene-3-carbaldehyde

To a 2-neck RB flask equipped with a condenser under nitrogen were added NBS (2.78 g), AIBN (102 mg), and benzene (21 mL). The mixture was stirred at 85° C. for 10 minutes and 3-methyl-2-oxo-2H-chromen-7-yl acetate (1.37 g) was added and stirring was continued overnight. Benzene was evaporated, NaOAc (4.62 g) and HOAc (20 mL) were added, and the mixture was stirred under reflux for 4 hrs, then partitioned in EtOAc and water. The organic layer was evaporated, the residue was stirred with 4N HCl for 30 minutes. The solid was collected, washed with ether and dried under vacuum. Yield: 75%.

(E)-7-hydroxy-3-(3-oxo-3-phenylprop-1-en-1-yl)-2H-chromen-2-one

To a RB flask were added acetophenone (63 mg, 0.52 mmol), 7-hydroxy-2-oxo-2H-chromene-3-carbaldehyde (100 mg, 0.52 mmol), and acetic acid (1 mL). The mixture was stirred to solution, 1 drop of conc. $H_2SO_4$ was added, and stirring was continued at 60° C. overnight. The mixture was cooled to rt and ethanol (2 mL) was added with continuous stirring. Five minutes later the solid was collected by filtration, washed with cold ethanol and ether, and dried under vacuum to give yellow solid. Yield: 60 mg, 32%.

Ethyl 4-(5-(7-hydroxy-2-oxo-2H-chromen-3-yl)-3-phenyl-4,5-dihydro-1H-pyrazol-1-yl)benzoate (E)-7-hydroxy-3-(3-oxo-3-phenylprop-1-en-1-yl)-2H-chromen-2-one (100 mg, 0.34 mmol), ethyl 4-hydrazinylbenzoate (74 mg, 0.41 mmol), acetic acid (164 mg, 2.72 mmol) and ethanol (3 mL) was stirred under reflux for 2 days. The resultant solid was collected by filtration and purified by column chromatography (silica gel, eluted with EtOAc/hexanes 1:2) to give yellow powder. Yield: 66 mg, 38%.

Example 4 (Formula IX)

Synthesis of ethyl 1,3-diphenyl-1H-pyrazole-4-carboxylate and N-benzyl-1,3-diphenyl-4,5-dihydro-1H-pyrazole-4-carboxamide

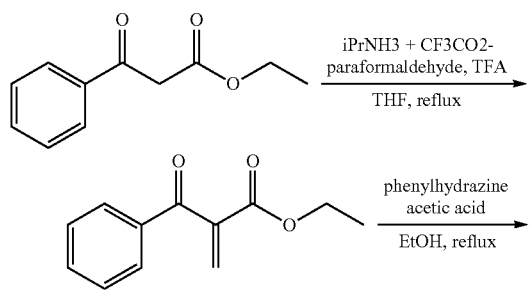

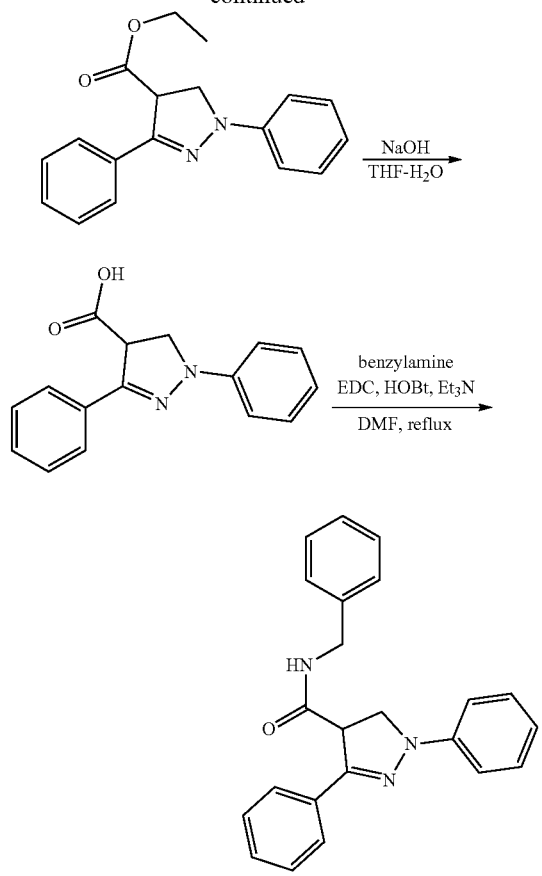

Ethyl 2-benzoylacrylate

Ethyl benzoylacetate (10.0 g, 52.0 mmol), diisopropylammonium trifluoroacetate (11.2 g, 52.0 mmol), TFA (0.4 mL, 5.2 mmol), and THF (150 mL) were placed in a 500 mL RB flask. Paraformaldehyde (6.2 g, 208.1 mmol as monomer) and THF (150 mL) were then added, and the reaction mixture was heated to reflux with stirring overnight. The resulting precipitate was removed by filtration and washed with ethyl acetate. The filtrate was combined with the wash and evaporated under reduced pressure. Column chromatography ($CH_2Cl_2$/hexane=1:2) of the crude product over silica gel gave a yellow liquid. Yield: 66%.

Ethyl 1,3-diphenyl-4,5-dihydro-1H-pyrazole-4-carboxylate

Ethyl 2-benzoylacrylate (6.3 g, 30.8 mmol), phenylhydrazine (3.3 g, 30.8 mmol), acetic acid (14.1 mL) and ethanol (61.7 mL) were placed in a 250 mL round-bottom flask. The reaction mixture was heated to reflux for 3 hours. After the reaction, the solvent was removed under reduced pressure. The resulting residue was extracted with dichloromethane, washed with brine, and dry with $MgSO_4$. Column chromatography ($CH_2Cl_2$:hexane=1:1) of the crude product over silica gel gave a yellow liquid. Yield: 70%.

1,3-Diphenyl-4,5-dihydro-1H-pyrazole-4-carboxylic acid

Ethyl 1,3-diphenyl-4,5-dihydro-1H-pyrazole-4-carboxylate (120 mg, 0.41 mmol) was dissolved in THF (0.7 mL) and NaOH (30 mg, 0.42 mmol), followed by H₂O (0.7 mL) was added. The mixture was stirred until reaction is complete. THF was evaporated. The residue was adjusted to pH2 with diluted HCl and extracted with EtOAc. The organic layers were dried (MgSO₄) and evaporated. The residue was triturated in CH₂Cl₂. Yield: 82%.

N-benzyl-1,3-diphenyl-4,5-dihydro-1H-pyrazole-4-carboxamide 1,3-Diphenyl-4,5-dihydro-1H-pyrazole-4-carboxylic acid (150 mg, 0.56 mmol), EDC (160 mg, 0.84 mmol) and HOBt (110 mg, 0.84 mmol) were dissolved in DMF (1.9 mL). Benzylamine (300 mg, 0.56 mmol) and triethylamine (0.16 mL, 1.13 mmol) were added. The mixture was allowed to react for 24 hr and then poured into water. The precipitate was collected, washed with water and recrystallized from CH₂Cl₂. Yield: 39%.

Example 5 (Formula XIII)

Synthesis of ethyl 4-(3-(6-methoxy-2-oxo-2H-chromen-3-yl)-1-phenyl-1H-pyrazol-5-yl)benzoate

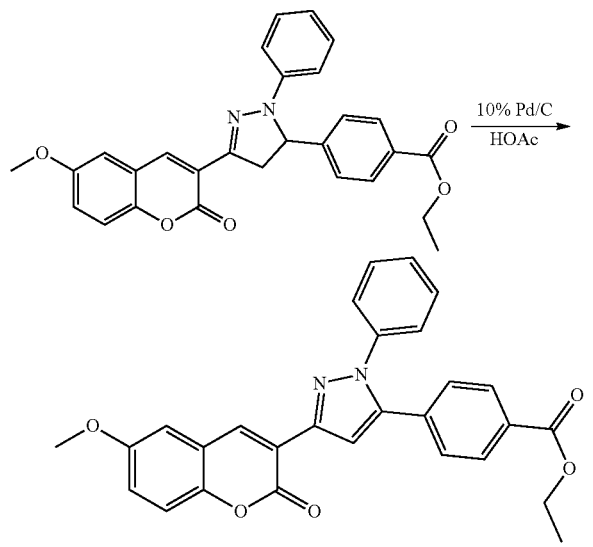

Ethyl 4-(3-(6-methoxy-2-oxo-2H-chromen-3-yl)-1-phenyl-4,5-dihydro-1H-pyrazol-5-yl) benzoate (100 mg, 0.21 mmol, made by a similar process as Example 1) was dissolved in acetic acid (1 mL) and 10% Pd—C (20 mg) was added. The mixture was heated to 80° C. and stirred for 6.5 hrs. The mixture was filtered through celite and the celite pad was washed with methanol. The filtrate was evaporated and triturated with 2 mL of methanol over 2 hr. The solid was collected by filtration, washed with cold methanol and ether, and dried under vacuum to give yellow powder. Yield: 50 mg, 50%.

Example 6 (Formula XVIII)

Synthesis of 3-(5-chloro-2,4-dihydroxyphenyl)-4-(4-methoxyphenyl)-N-phenyl-1H-pyrazole-5-carboxamide

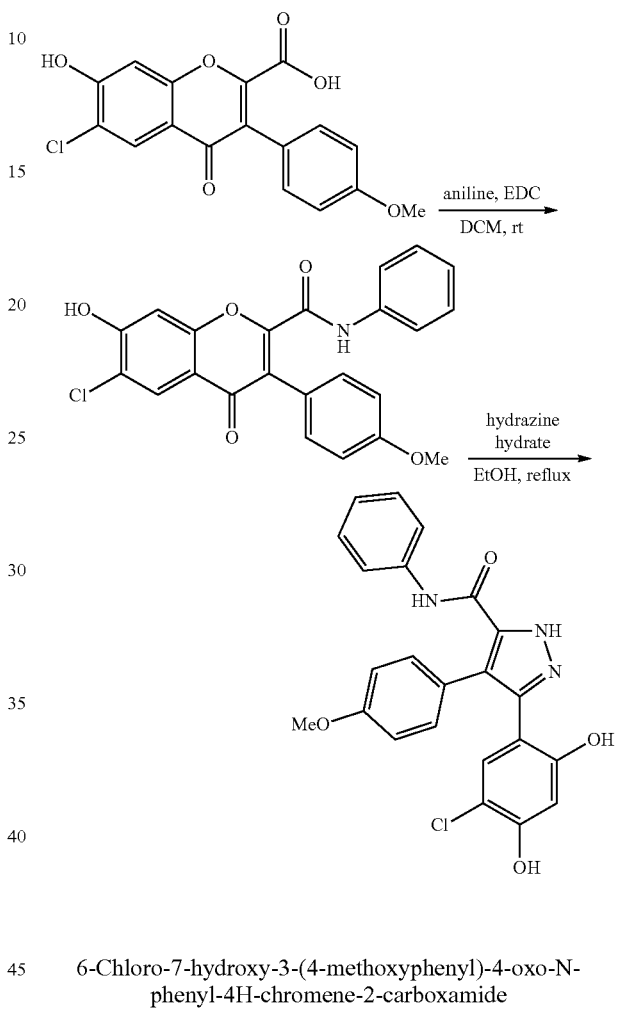

6-Chloro-7-hydroxy-3-(4-methoxyphenyl)-4-oxo-N-phenyl-4H-chromene-2-carboxamide 6-Chloro-7-hydroxy-3-(4-methoxyphenyl)-4-oxo-4H-chromene-2-carboxylic acid (0.20 g, 0.58 mmol, for synthesis see Dymock, B., J. Med. Chem. 2005, 48, 4212-4215), EDC (0.17 g, 0.87 mmol), CH₂Cl₂ (2 mL), and aniline (0.13 g, 1.44 mmol) were placed in a 5.0 mL RB flask. The reaction mixture was stirred overnight. The precipitate was collected by filtration, washed with cold water and ether and dried under vacuum. Yield: 100 mg, 41%.

3-(5-Chloro-2,4-dihydroxyphenyl)-4-(4-methoxyphenyl)-N-phenyl-1H-pyrazole-5-carboxamide 6-Chloro-7-hydroxy-3-(4-methoxyphenyl)-4-oxo-N-phenyl-4H-chromene-2-carboxamide (0.10 g, 0.24 mmol), hydrazine hydrate (0.1 mL), and ethanol (2.3 mL) were placed in a 5.0 mL RB flask. The mixture was heated to reflux with stirring overnight. The solvent was removed under reduced pressure. The residue was washed with cold water and ether and dried under vacuum. Yield: 90 mg, 90%.

Example 7

Anti-Angiogenic Activity of Sunitinib

Zebrafish embryos were collected and washed with RO water prior to 2 hours post fertilization (hpf) and then incubated in RO water at 28° C. until 24 hpf. Embryos were placed into 4 single wells of a 24-well plate with five embryos per well. Each well was treated respectively with 1 mL of either 0.05% DMSO as control or Sunitinib in one of three concentrations: 5 µM, 2.5 µM, and 1 µM in water. In one variation of this experiment, phenylthiourea (PTU) was co-administered to a final concentration of 200 µM to inhibit embryonic pigmentation. The plate was incubated for additional 48 hours, the liquid in each well was removed and the embryos were washed with 1 mL of water. 4-(5-(4-(Ethoxycarbonyl)phenyl)-3-(6-methoxy-2-oxo-2H-chromen-3-yl)-4,5-dihydro-1H-pyrazol-1-yl)benzoic acid (1 mL at 20 µM) was added to each well and the plate was incubated at 28° C. for one hour. The liquid in each well was removed and the embryos were washed with 1 mL of water. The embryos were picked up one by one using a pipette, each placed on a glass slide, and temporarily anesthetized with 10 µL of 7.5% tricaine (MS-222). The embryo was embedded in 20 µL of 3% methyl cellulose and imaged using a Zeiss M2 microscope and the Axiocam HRC image system.

We claim:

1. A method of visualizing and imaging blood vessels or blood flow in a test subject wherein the test subject is a selected part or the entirety of a dead or living animal, including a human, comprising;
    a) administering fluorescent compounds to the test subject to achieve inclusion of the fluorescent compounds in the test subject's blood vessels and/or blood serum wherein the fluorescent compounds are selected from;
    4-(3-(6-Methoxy-2-oxo-2H-chromen-3-yl)-5-phenyl-4,5-dihydro-1H-pyrazol-1-yl)benzoic acid,
    4-(3-(7-(3-Bromopropoxy)-2-oxo-2H-chromen-3-yl)-5-phenyl-4,5-dihydro-1H-pyrazol-1-yl)benzoic acid,
    (11-((4-(3-(6-Methoxy-2-oxo-2H-chromen-3-yl)-5-phenyl-4,5-dihydro-1H-pyrazol-1-yl)benzoyl)oxy)undecyl)triphenylphosphonium,
    Ethyl 4-(3-(6-methoxy-2-oxo-2H-chromen-3-yl)-5-phenyl-4,5-dihydro-1H-pyrazol-1-yl)benzoate,
    5-Chloropentyl 4-(3-(6-methoxy-2-oxo-2H-chromen-3-yl)-5-phenyl-4, 5-dihydro-1H-pyrazol-1-yl)benzoate,
    (3R,4R, 5S,6R)-6-(Acetoxymethyl)-3-(4-(3-(6-methoxy-2-oxo-2H-chromen-3-yl)-5-phenyl-4,5-dihydro-1H-pyrazol-1-yl)benzamido)tetrahydro-2H-pyran-2,4,5-triyl triacetate,
    4-(3-(6-Methoxy-2-oxo-2H-chromen-3-yl)-1-phenyl-4,5-dihydro-1H-pyrazol-5-yl)benzoic acid,
    (3-((3-(1-(4-Carboxyphenyl)-5-phenyl-4,5-dihydro-1H-pyrazol-3-yl)-2-oxo-2H-chromen-7-yl)oxy)propyl)triphenylphosphonium,
    Ethyl 4-(3-(6-methoxy-2-oxo-2H-chromen-3-yl)-1-phenyl-4,5-dihydro-1H-pyrazol-5-yl)benzoate, 2,5-Dioxopyrrolidin-1-yl 4-(3-(6-methoxy-2-oxo-2H-chromen-3-yl)-5-phenyl-4,5-dihydro-1H-pyrazol-1-yl)benzoate,
    4-(3-(6-Methoxy-2-oxo-2H-chromen-3-yl)-5-phenyl-4,5-dihydro-1H-pyrazol-1-yl)-N-((3R,4R,5S,6R)-2,4,5-trihydroxy-6-(hydroxymethyl)tetrahydro-2H-pyran-3-yl)benzamide,
    3-(1-(4-Fluorophenyl)-5-phenyl-4,5-dihydro-1H-pyrazol-3-yl)-6-methoxy-2H-chromen-2-one,
    (3-((4-(3-(6-Methoxy-2-oxo-2H-chromen-3-yl)-1-phenyl-4,5-dihydro-1H-pyrazol-5-yl)benzoyl)oxy)propyl)triphenylphosphonium,
    (Z)-5((5-Fluoro-2-oxoindolin-3-ylidene)methyl)-N-(2-(4-(3-(6-methoxy-2-oxo-2H-chromen-3-yl)-5-phenyl-4,5-dihydro-1H-pyrazol-1-yl)benzamido)ethyl)-2,4-dimethyl-1H-pyrrole-3-carboxamide,
    Diethyl 4,4'-(3-(6-methoxy-2-oxo-2H-chromen-3-yl)-4,5-dihydro-1H-pyrazole-1,5-diyl)dibenzoate,
    3-(2-(5-((3aS,4S,6aR)-2-Oxohexahydro-1H-thieno[3,4-d]imidazol-4-yl)pentanoyl)hydrazinyl)propyl 4-(3-(6-methoxy-2-oxo-2H-chromen-3-yl)-5-phenyl-4,5-dihydro-1H-pyrazol-1-yl)benzoate hydrochloride,
    3-Bromopropyl 4-(3-(6-methoxy-2-oxo-2H-chromen-3-yl)-1-phenyl-4, 5-dihydro-1H-pyrazol-5-yl)benzoate,
    (Z)-3-((2-(5-((5-Fluoro-2-oxoindolin-3-ylidene)methyl)-2,4-dimethyl-1H-pyrrole-3-carboxamido)ethyl)amino) propyl 4-(3-(6-methoxy-2-oxo-2H-chromen-3-yl)-5-phenyl-4,5-dihydro-1H-pyrazol-1-yl)benzoate hydrochloride,
    4-(5-(4-(Ethoxycarbonyl)phenyl)-3-(6-methoxy-2-oxo-2H-chromen-3-yl)-4, 5-dihydro-1H-pyrazol-1-yl)benzoic acid,
    4-(3-(6-Methoxy-2-oxo-2H-chromen-3-yl)-5-phenyl-4,5-dihydro-1H-pyrazol-1-yl)-N'-(5-((3aS,4S,6aR)-2-oxohexahydro-1H-thieno[3,4-d]imidazol-4-yl)pentanoyl)benzohydrazide,
    Ethyl 4-(5-(3,4-dimethoxyphenyl)-3-(6-methoxy-2-oxo-2H-chromen-3-yl)-4,5-dihydro-1H-pyrazol-1-yl)benzoate, and Ethyl 3-(7-hydroxy-2-oxo-2H-chromen-3-yl)-1,5-diphenyl-4,5-dihydro-1H-pyrazole-4-carboxylate;
    and pharmaceutically acceptable salts, solvates, enantiomers, non-covalent complexes, and mixtures thereof, or pharmaceutical formulations containing the compound;
    b) irradiating an observation area of choice in the animal with a light source to excite the included fluorescent compounds;
    c) revealing of blood vessels, or motion of blood flow in the animal when the fluorescent compounds emit fluorescence, and;
    d) observing and recording fluorescent images of the blood vessels or blood flow with a microscope or a camera.

2. A method of claim 1 wherein the test subject is a zebrafish.

3. A method to identify, select, characterize, or collectively screen for substances that inhibit or promote blood vessel formation or angiogenesis in living, wild type or genetically altered zebrafish, comprising;
    a) exposing a test zebrafish to a selected substance or mixture of substances under a pre-determined set of conditions appropriate for the interaction between the substance(s) and a zebrafish, followed by;
    b) subjecting the zebrafish to the method in claim 2, and;
    c) examining the resulting images of blood vessels or blood flow to determine the effect on zebrafish blood vessel formation, or angiogenesis, caused by the selected substance(s).

* * * * *